United States Patent
Kessler et al.

(10) Patent No.: US 11,083,704 B2
(45) Date of Patent: Aug. 10, 2021

(54) METHOD OF ADMINISTERING NITROXYL DONATING COMPOUNDS

(71) Applicant: Cardioxyl Pharmaceuticals, Inc., Chapel Hill, NC (US)

(72) Inventors: Paul D. Kessler, Hagerstown, MD (US); William R. Ewing, Yardley, PA (US); Maria Borentain, Louveciennes (FR); Tushar Garimella, Skillman, NJ (US); Elyse G. Stock, Woodbridge, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/475,672

(22) PCT Filed: Jan. 2, 2018

(86) PCT No.: PCT/US2018/012114
§ 371 (c)(1),
(2) Date: Jul. 2, 2019

(87) PCT Pub. No.: WO2018/128999
PCT Pub. Date: Jul. 12, 2018

(65) Prior Publication Data
US 2019/0343790 A1 Nov. 14, 2019

Related U.S. Application Data

(60) Provisional application No. 62/441,803, filed on Jan. 3, 2017, provisional application No. 62/549,932, filed on Aug. 24, 2017.

(51) Int. Cl.
| | | |
|---|---|---|
| *A61K 31/341* | (2006.01) | |
| *A61P 9/04* | (2006.01) | |
| *A61K 9/00* | (2006.01) | |
| *A61K 47/02* | (2006.01) | |
| *A61K 47/24* | (2006.01) | |
| *A61K 47/40* | (2006.01) | |

(52) U.S. Cl.
CPC .......... *A61K 31/341* (2013.01); *A61K 9/0019* (2013.01); *A61K 47/02* (2013.01); *A61K 47/24* (2013.01); *A61K 47/40* (2013.01); *A61P 9/04* (2018.01)

(58) Field of Classification Search
CPC .................................................... A61K 31/341
See application file for complete search history.

(56) References Cited

U.S. PATENT DOCUMENTS

| | | |
|---|---|---|
| 6,936,639 B2 | 8/2005 | Wink et al. |
| 7,696,373 B2 | 4/2010 | King |
| 7,863,262 B2 | 1/2011 | Wink et al. |
| 7,989,652 B2 | 8/2011 | King |
| 8,030,356 B2 | 10/2011 | Toscano et al. |
| 8,227,639 B2 | 7/2012 | Toscano et al. |
| 8,268,890 B2 | 9/2012 | Wink et al. |
| 8,269,034 B2 | 9/2012 | King |
| 8,318,705 B2 | 11/2012 | Frost et al. |
| 8,569,536 B2 | 10/2013 | King |
| 8,674,132 B2 | 3/2014 | Toscano et al. |
| 8,791,134 B2 | 7/2014 | Frost et al. |
| RE45,314 E | 12/2014 | Toscano et al. |
| 8,987,326 B2 | 3/2015 | Kalish et al. |
| 9,018,411 B2 | 4/2015 | Toscano et al. |
| 9,115,064 B2 | 8/2015 | Toscano et al. |
| 9,156,804 B2 | 10/2015 | Kalish et al. |
| 9,181,213 B2 | 11/2015 | Toscano et al. |
| 9,221,780 B2 | 12/2015 | Toscano et al. |
| 9,458,127 B2 | 10/2016 | Toscano et al. |
| 9,487,498 B2 | 11/2016 | Toscano et al. |
| 9,499,511 B2 | 11/2016 | Toscano et al. |
| 9,586,896 B2 | 3/2017 | Kalish et al. |
| 9,617,208 B2 | 4/2017 | Toscano et al. |
| 9,676,708 B2 | 6/2017 | Toscano et al. |
| 9,682,938 B2 | 6/2017 | Kalish et al. |
| 9,725,402 B2 | 8/2017 | Frost et al. |
| 9,725,410 B2 | 8/2017 | Toscano et al. |
| 9,732,029 B2 | 8/2017 | Frost et al. |
| 9,862,699 B2 | 1/2018 | Toscano et al. |
| 9,932,303 B2 | 4/2018 | Kalish et al. |
| 9,968,584 B2 | 5/2018 | Kalish et al. |
| 9,969,684 B2 | 5/2018 | Toscano et al. |
| 1,021,340 A1 | 2/2019 | Kalish et al. |
| 1,024,524 A1 | 4/2019 | Kalish et al. |
| 1,017,976 A1 | 11/2019 | Toscano et al. |
| 1,048,704 A1 | 11/2019 | Toscano et al. |

(Continued)

FOREIGN PATENT DOCUMENTS

| | | |
|---|---|---|
| WO | WO2007109175 | 9/2007 |
| WO | WO2014113696 | 7/2014 |
| WO | WO2014113700 | 7/2014 |

OTHER PUBLICATIONS

Tita, C. et al., "A Phase 2a Dose-Escalation Study of the Safety, Tolerability, Pharmacokinetics and Haemodynamic Effects of BMS-986231 in Hospitalized Patients with Heart Failure with Reduced Ejection Fraction," European Journal of Heart Failure, vol. 19, Jul. 5, 2017, pp. 1321-1332.

"Cardioxyl Pharmaceuticals Presents Data on Its Clinical Candidate, CXL-1020, at the 60th Annual American College of Cardiology Scientific Session", Apr. 4, 2011, http://www.evaluategroup.com.

Cowart, Doug et al., A Phase 1 Study of the Safety and Pharmacokinetics of the Intravenous Nitroxyl Prodrug, CXL-1427 In JACC, vol. 65, Issue 10S, Mar. 17, 2015.

(Continued)

*Primary Examiner* — Karen Cheng
(74) *Attorney, Agent, or Firm* — Byrne Poh LLP; Nina R. Horan

(57) ABSTRACT

The disclosed subject matter provides methods of using nitroxyl donating compounds and pharmaceutical compositions comprising such compounds in a dose escalation regimen.

27 Claims, No Drawings

(56) References Cited

U.S. PATENT DOCUMENTS

| | | |
|---|---|---|
| 1,051,784 A1 | 12/2019 | Kalish et al. |
| 10,548,872 B2 | 2/2020 | Kalish et al. |
| 1,058,314 A1 | 3/2020 | Toscano et al. |
| 10,792,273 B2 | 10/2020 | Kalish et al. |
| 2004/0038947 A1 | 2/2004 | Wink et al. |
| 2009/0281067 A1 | 11/2009 | Toscano et al. |
| 2009/0298795 A1 | 12/2009 | Paolocci et al. |
| 2011/0081427 A1 | 4/2011 | Wink et al. |
| 2011/0144067 A1 | 6/2011 | Toscano et al. |
| 2011/0160200 A1 | 6/2011 | Mazhari et al. |
| 2011/0306614 A1 | 12/2011 | Toscano et al. |
| 2012/0201907 A1 | 8/2012 | Wink et al. |
| 2014/0235636 A1 | 8/2014 | Toscano et al. |
| 2015/0004259 A1 | 1/2015 | Wink et al. |
| 2015/0141378 A1 | 5/2015 | Toscano et al. |
| 2016/0046570 A1 | 2/2016 | Toscano et al. |
| 2016/0060229 A1 | 3/2016 | Toscano et al. |
| 2016/0081951 A1 | 3/2016 | Mazhari et al. |
| 2016/0166604 A1 | 6/2016 | Paolocci et al. |
| 2016/0228460 A1 | 8/2016 | Wink et al. |
| 2018/0050985 A1 | 2/2018 | Toscano et al. |
| 2018/0305304 A1 | 10/2018 | Kalish et al. |
| 2018/0318308 A1 | 11/2018 | Kalish et al. |
| 2019/0161464 A1 | 5/2019 | Toscano et al. |
| 2020/0087253 A1 | 3/2020 | Toscano et al. |
| 2020/0121633 A1 | 4/2020 | Kalish et al. |
| 2020/0163929 A1 | 5/2020 | Kalish et al. |

OTHER PUBLICATIONS

International Preliminary Report on Patentability dated Jul. 18, 2019 in International Patent Application No. PCT/US2018/012114.
International Search Report and Written Opinion dated Apr. 10, 2018 in International Patent Application No. PCT/US2018/012114.
Office Action dated Nov. 16, 2020 in EP Patent Application No. 18705193.3, pp. 1-4.

METHOD OF ADMINISTERING NITROXYL DONATING COMPOUNDS

1. BACKGROUND

Nitroxyl (HNO) has been shown to have positive cardiovascular effects in in vitro and in vivo models of failing hearts. However, at physiological pH, HNO dimerizes to hyponitrous acid, which subsequently dehydrates to nitrous oxide; due to this metastability, HNO for therapeutic use must be generated in situ from donor compounds. A variety of compounds capable of donating nitroxyl have been described and proposed for use in treating disorders known or suspected to be responsive to nitroxyl. See, e.g., U.S. Pat. Nos. 6,936,639; 7,696,373; 8,030,356; 8,268,890; 8,227,639; 8,318,705; 8,987,326 and 9,464,061; and U.S. pre-grant publication nos. 2009/0281067; 2009/0298795; 2011/0136827; 2011/0144067; 2015/36697; and 2015/0344437.

U.S. Pat. No. 8,987,326 describes nitroxyl donating compounds that are highly efficacious in treating cardiovascular diseases (e.g., heart failure) and have suitable toxicological profiles. One such nitroxyl donor, N-hydroxy-5-methylfuran-2-sulfonamide has been evaluated in preclinical models and in Phase I/IIa studies. In these studies, N-hydroxy-5-methylfuran-2-sulfonamide demonstrated peripheral vasodilation and increased inotropy and improved lusitropy. Cowart D, Venuti R, Guptill J, Noveck R, Foo S. A phase 1 study of the safety and pharmacokinetics of the intravenous nitroxyl prodrug, CXL-1427. *J Am Coll Cardiol* 2015 65 A876; European Heart Failure 2016 Congress in Florence, Italy, May 21-24, 2016; and *Eur J Heart Fail.* 2017 Oct. 19(10):1321-1332. Infusions of N-hydroxy-5-methylfuran-2-sulfonamide, in the Phase I and Phase IIa studies, were found to be safe and well-tolerated in healthy patients and in patients hospitalized with advanced heart failure. The effect of an infusion of a nitroxyl donating compound on blood pressure may consist of a balance of blood pressure lowering due to vasodilation and maintained blood pressure due to enhanced contractility secondary to due to positive inotropic effect. Therefore, such infusions could result in overall decreases in blood pressure (hypotension), and excessive hypotension is generally viewed as unfavorable.

Accordingly, there is an unmet clinical need for a method of administering nitroxyl donating compounds to a patient that eliminates, minimizes or reduces the risk of adverse events, such as hypotension, and other undesirable side effects.

Citation of any reference in Section 1 of this application is not to be construed as an admission that such reference is prior art to the present application.

2. SUMMARY OF THE DISCLOSURE

The present disclosure overcomes the unmet clinical need by providing a dose escalation regimen for the administration of a nitroxyl donating compound. The dose escalation regimen of the present disclosure provides a nitroxyl donating compound, or a pharmaceutical composition comprising a nitroxyl donating compound and at least one pharmaceutically acceptable excipient, in an amount that the final dosage is not reached for at least 2 hours. In one embodiment, the final dosage of the nitroxyl donating compound is not reached for at least 4 hours. In another embodiment, the final dosage of the nitroxyl donating compound is not reached for at least 6 hours. In another embodiment, the final dosage of the nitroxyl donating compound is not reached for at least 8 hours. In another embodiment, the final dosage of the nitroxyl donating compound is not reached for at least 10 hours. In another embodiment, the final dosage of the nitroxyl donating compound is not reached for at least 12 hours. In another embodiment, the final dosage of the nitroxyl donating compound is not reached until about 2 hours. In another embodiment, the final dosage of the nitroxyl donating compound is not reached until about 4 hours. In another embodiment, the final dosage of the nitroxyl donating compound is not reached until about 6 hours. In another embodiment, the final dosage of the nitroxyl donating compound is not reached until about 8 hours. In another embodiment, the final dosage of the nitroxyl donating compound is not reached until about 10 hours. In another embodiment, the final dosage of the nitroxyl donating compound is not reached until about 12 hours. The methods of the present disclosure are designed to eliminate, minimize or reduce the risk of adverse events associated with the use of the nitroxyl donating compound.

The present disclosure provides a method of administering nitroxyl therapy to a patient comprising administering an initial dosage of a nitroxyl donating compound, or a pharmaceutical composition comprising a nitroxyl donating compound and at least one pharmaceutically acceptable excipient, in a first amount for the duration of a first period of time; optionally administering a second dosage of a nitroxyl donating compound, or a pharmaceutical composition comprising a nitroxyl donating compound and at least one pharmaceutically acceptable excipient, in a second amount for the duration of a second period of time; and administering a final dosage of a nitroxyl donating compound, or a pharmaceutical composition comprising a nitroxyl donating compound and at least one pharmaceutically acceptable excipient, in a final amount for the duration of a final period of time.

In a particular embodiment, a nitroxyl donating compound used in the methods of the disclosure is a compound of the formula (1):

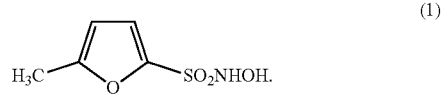

(1)

In another embodiment, a nitroxyl donating compound used in the methods of the disclosure is a compound of the formula (2):

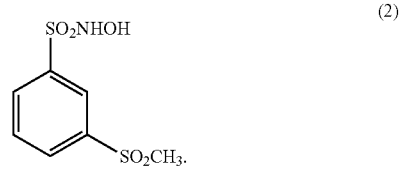

(2)

It will be understood that the term "nitroxyl donating compound" includes both compounds with a free N-hydroxy group (e.g., compounds of formula (1) or (2)) and compounds in which the N-hydroxy group is esterified, as depicted below:

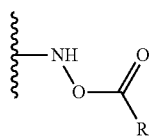

(99)

where ⁞ represents the aromatic, heteroaromatic or heterocyclic portion of the compound (see Section 3.3 for definitions of R).

3. DETAILED DESCRIPTION

The invention includes the following:
(1) An initial dose escalation regimen method for administering nitroxyl therapy to a patient for the treatment of a cardiovascular disease comprising:
administering intravenously a nitroxyl donating compound, or a pharmaceutical composition comprising a nitroxyl donating compound and at least one pharmaceutically acceptable excipient, to a patient at a first dosage amount for the duration of a first period of the dose escalation regimen;
optionally administering intravenously the nitroxyl donating compound, or the pharmaceutical composition comprising the nitroxyl donating compound and at least one pharmaceutically acceptable excipient, to the patient at a second dosage amount for the duration of a second period of the dose escalation regimen; and
administering intravenously the nitroxyl donating compound, or the pharmaceutical composition comprising the nitroxyl donating compound and at least one pharmaceutically acceptable excipient, to the patient at a final dosage amount for the duration of a final period of the dose escalation regimen, wherein the patient is administered nitroxyl therapy for the treatment of a cardiovascular disease.
(2) The method of the above (1), wherein the cardiovascular disease is heart failure.
(3) The method of the above (2), wherein the cardiovascular disease is acute decompensated heart failure.
(4) The method of any one of the above (1) to (3), wherein the first dosage amount is in the range of about 1 µg/kg/min to about 9 µg/kg/min.
(5) The method of any one of the above (1) to (3), wherein the first dosage amount is about 3 µg/kg/min.
(6) The method of claim any one of the above (1) to (3), wherein the first dosage amount is about 6 µg/kg/min.
(7) The method of any one of the above (1) to (6), wherein the second dosage amount is in the range of about 3 µg/kg/min to about 12 µg/kg/min.
(8) The method of any one of the above (1) to (6), wherein the second dosage amount is about 6 µg/kg/min.
(9) The method of any one of the above (1) to (8), wherein the final dosage amount is in the range of about 4 µg/kg/min to about 24 µg/kg/min.
(10) The method of any one of the above (1) to (8), wherein the final dosage amount is about 12 µg/kg/min.
(11) The method of any one of the above (1) to (10), wherein the first period of time is in the range of about 1 hour to about 6 hours.
(12) The method of any one of the above (1) to (10), wherein the first period of time is about 4 hours.
(13) The method of any one of the above (1) to (12), wherein the second period of time is in the range of about 1 hour to about 6 hours.
(14) The method of any one of the above (1) to (12), wherein the second period of time is about 4 hours.
(15) The method of any one of the above (1) to (14), wherein the final period of time is in the range of about 4 hours to about 168 hours.
(16) The method of any one of the above (1) to (14), wherein the final period of time is about 40 hours.
(17) The method of any one of the above (1) to (14), wherein the final period of time is about 44 hours.
(18) The method of any one of the above (1) to (3), comprising:
administering intravenously the nitroxyl donating compound, or the pharmaceutical composition comprising the nitroxyl donating compound and at least one pharmaceutically acceptable excipient, to the patient in an amount of about 6 µg/kg/min for about 4 hours; and
administering intravenously the nitroxyl donating compound, or the pharmaceutical composition comprising the nitroxyl donating compound and at least one pharmaceutically acceptable excipient, to the patient in an amount of about 12 µg/kg/min for about 44 hours.
(19) The method of any one of the above (1) to (3), comprising:
administering intravenously a nitroxyl donating compound, or a pharmaceutical composition comprising a nitroxyl donating compound and at least one pharmaceutically acceptable excipient, to a patient in an amount of about 3 µg/kg/min for about 4 hours;
administering intravenously the nitroxyl donating compound, or the pharmaceutical composition comprising the nitroxyl donating compound and at least one pharmaceutically acceptable excipient, to the patient in an amount of about 6 µg/kg/min for about 4 hours; and
administering intravenously the nitroxyl donating compound, or the pharmaceutical composition comprising the nitroxyl donating compound and at least one pharmaceutically acceptable excipient, to the patient in an amount of about 12 µg/kg/min for about 40 hours.
(20) The method of any one of the above (1) to (19), wherein the dose escalation regimen eliminates, minimizes or reduces the risk of hypotension.
(21) The method of any one of the above (1) to (20), wherein the nitroxyl donating compound is a compound of formula (1):

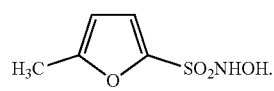

(1)

(22) The method of any one of the above (1) to (20), wherein the nitroxyl donating compound is a compound of formula (2):

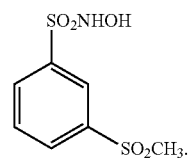

(2)

(23) The method of any one of the above (1) to (22), wherein the composition is formulated at a pH of from about 5 to about 6.

(24) The method of any one of the above (1) to (22), wherein the composition is formulated at a pH of from about 5.5 to about 6.2.
(25) The method of any one of the above (1) to (22), wherein the composition is formulated at a pH of from about 6.
(26) The method of any one of the above (1) to (25), wherein the at least one pharmaceutically acceptable excipient is a buffering agent.
(27) The method of the above (26), wherein the buffering agent is potassium acetate.
(28) The method of the above (26), wherein the buffering agent is potassium phosphate.
(29) The method of any one of the above (1) to (28), further comprising a stabilizing agent.
(30) The method of the above (29), wherein the stabilizing agent is a cyclodextrin.
(31) The method of the above (30), wherein the cyclodextrin is a sulfo-n-butyl ether derivative of β-cyclodextrin having six or seven sulfo-n-butyl ether groups per cyclodextrin molecule.
(32) The method of the above (30) or (31), wherein the cyclodextrin is CAPTISOL®.
(33) The method of any one of the above (30) to (32), wherein the molar ratio between the nitroxyl donating compound and the cyclodextrin present in the composition is from about 0.02:1 to about 2:1.
(34) The method of any one of the above (30) to (32), wherein the molar ratio between the nitroxyl donating compound and the cyclodextrin present in the composition is from about 0.05:1 to about 1.5:1.
(35) The method of any one of the above (30) to (32), wherein the molar ratio between the nitroxyl donating compound and the cyclodextrin present in the composition is from about 0.5:1 to about 1:1.
(36) The method of any one of the above (1) to (22), wherein the at least one pharmaceutically acceptable excipient is a cyclodextrin.
(37) The method of the above (36), wherein the cyclodextrin is a sulfo-n-butyl ether derivative of β-cyclodextrin having six or seven sulfo-n-butyl ether groups per cyclodextrin molecule.
(38) The method of the above (36) or (37), wherein the cyclodextrin is CAPTISOL®.
(39) The method of any one of the above (36) to (38), wherein the molar ratio between the nitroxyl donating compound and the cyclodextrin present in the composition is from about 0.02:1 to about 2:1.
(40) The method of any one of the above (36) to (38), wherein the molar ratio between the nitroxyl donating compound and the cyclodextrin present in the composition is from about 0.05:1 to about 1.5:1.
(41) The method of any one of the above (36) to (38), wherein the molar ratio between the nitroxyl donating compound and the cyclodextrin present in the composition is from about 0.5:1 to about 1:1.
(42) A method of reducing the risk of an adverse event in a patient receiving nitroxyl therapy for the treatment of cardiovascular disease, comprising use of an initial dose escalation regimen comprising the steps of:
administering intravenously a nitroxyl donating compound, or a pharmaceutical composition comprising a nitroxyl donating compound and at least one pharmaceutically acceptable excipient, to a patient at a first dosage amount for the duration of a first period of the dose escalation regimen;
optionally administering intravenously the nitroxyl donating compound, or the pharmaceutical composition comprising the nitroxyl donating compound and at least one pharmaceutically acceptable excipient, to the patient at a second dosage amount for the duration of a second period of the dose escalation regimen; and
administering intravenously the nitroxyl donating compound, or the pharmaceutical composition comprising the nitroxyl donating compound and at least one pharmaceutically acceptable excipient, to the patient at a third dosage amount for the duration of a final period of the dose escalation regimen, wherein the patient is administered nitroxyl therapy for the treatment of a cardiovascular disease.
(43) The method of the above (42), wherein the cardiovascular disease is heart failure.
(44) The method of the above (43), wherein the cardiovascular disease is acute decompensated heart failure.
(45) The method of any one of the above (42) to (44), wherein the nitroxyl donating compound is a compound of formula (1):

$$\underset{H_3C}{\underset{}{\bigcirc}}\!\!-\!\!SO_2NHOH. \tag{1}$$

46. The method of any one of the above (42) to (44), wherein the nitroxyl donating compound is a compound of formula (2):

$$\underset{}{\bigcirc}\!\!\begin{matrix}SO_2NHOH\\\\SO_2CH_3.\end{matrix} \tag{2}$$

3.1 Definitions

Unless clearly indicated otherwise, the following terms as used herein have the meanings indicated below.

A "pharmaceutically acceptable salt" refers to a salt of any therapeutic agent disclosed herein, which salt can include any of a variety of organic and inorganic counter ions known in the art and which salt is pharmaceutically acceptable. When the therapeutic agent contains an acidic functionality, various exemplary embodiments of counter ions are sodium, potassium, calcium, magnesium, ammonium, tetraalkylammonium, and the like. When the therapeutic agent contains a basic functionality, a pharmaceutically acceptable salt can include as a counter ion, by way of example, an organic or inorganic acid, such as hydrochloride, hydrobromide, tartrate, mesylate, acetate, maleate, oxalate, and the like. Illustrative salts include, but are not limited to, sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucaronate, saccharate, formate, benzoate, glutamate, methanesulfonate, ethanesulfonate, benzenesulfonate, and p-toluenesulfonate salts. Accordingly, a salt can be prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl-N-ethylamine; diethylamine; triethylamine; mono-, bis-, or tris-(2-hydroxy-lower-alkyl amines), such as mono-, bis-, or tris-(2-hydroxyethyl)amine, 2-hydroxy-tert-butylamine, or tris-(hydroxymethyl)methylamine, N,N-di-lower-alkyl-N-(hydroxy-lower-alkyl)-amines, such as N,N-dimethyl-N-(2-hydroxyethyl) amine, or tri-(2-hydroxyethyl)amine; N-methyl-D-glucamine; and amino acids such as arginine, lysine, and the like. A salt can also be prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

"Pharmaceutically acceptable excipient" refers to any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or pharmaceutical composition into a unit dosage form for administration. Pharmaceutically acceptable excipients are known in the pharmaceutical arts and are disclosed, for example, in Gennaro, Ed., *Remington: The Science and Practice of Pharmacy*, 20$^{th}$ Ed. (Lippincott Williams & Wilkins, Baltimore, Md., 2000) and *Handbook of Pharmaceutical Excipients*, American Pharmaceutical Association, Washington, D.C., (e.g., 1$^{st}$, 2$^{nd}$ and 3$^{rd}$ Eds., 1986, 1994 and 2000, respectively). As will be known to those in the art, pharmaceutically acceptable excipients can provide a variety of functions and can be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as dextrose, lactose, glucose and sucrose; (2) starches, such as corn starch and potato starch; (3) cellulose and its derivatives, such as sodium carboxymethyl cellulose, ethyl cellulose, cellulose acetate, hydroxypropylmethylcellulose, and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as potassium acetate, magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Unit dosage form" refers to a physically discrete unit suitable as a unitary dosage for a human or an animal. Each unit dosage form can contain a predetermined amount of a therapeutic agent calculated to produce a desired effect.

Unless clearly indicated otherwise, a "patient" refers to an animal, such as a mammal, including but not limited to, a human. Hence, the methods disclosed herein can be useful in human therapy and veterinary applications. In particular embodiments, the patient is a mammal. In certain embodiments, the patient is a human.

"Therapeutically effective amount" refers to such amount of a therapeutic agent or a pharmaceutically acceptable salt thereof, which in combination with its parameters of efficacy and potential for toxicity, as well as based on the knowledge of the practicing specialist, should be effective in a given therapeutic form. As is understood in the art, an effective amount can be administered in one or more doses.

"Treat", "treating" or "treatment" cover a treatment of a disease-state in a mammal, particularly in a human, and include: inhibiting a disease-state, i.e., arresting it development; and/or relieving a disease-state, i.e., causing regression of a disease state; and/or to reduce and/or minimize the risk; and/or reduction in the risk of recurrence of a disease state even if conditions of the clinical disease state may or may not be presented yet. Treatment can be treatment to reduce or minimize the risk of a disease state in a patient that has not yet presented with a clinical disease state and/or treatment to minimize or reduce the risk of a recurrence.

"Prevent", "preventing" and the like covers the preventive treatment of a subclinical disease-state in a mammal, particularly in a human, aimed at reducing the probability of the occurrence of a clinical disease-state. Patients may be selected for preventative therapy based on factors that are known to increase risk of suffering a clinical disease state compared to the general population.

A condition that is "responsive to nitroxyl therapy" includes any condition in which administration of a compound that donates an effective amount of nitroxyl under physiological conditions treats and/or prevents the condition, as those terms are defined herein. A condition whose symptoms are suppressed or diminished upon administration of nitroxyl donor is a condition responsive to nitroxyl therapy.

"Pulmonary hypertension" or "PH" refers to a condition in which the pulmonary arterial pressure is elevated. The current hemodynamic definition of PH is a mean pulmonary arterial pressure (MPAP) at rest of greater than or equal to 25 mmHg. Badesch et al., *J. Amer. Coll. Cardiol.* 54(Suppl.): S55-S66 (2009).

"Clinically relevant hypotension" is defined by SBP <90 mg or symptoms of hypotension, during infusion and up to 6 hours after the final infusion has ended. Hypotension can be assessed by a collection of signs, symptoms and blood pressure measurements.

"Symptomatic hypotension" refers to the presence of both low SBP and significant and/or non-resolving systems due to low blood pressure (e.g., lightheadedness, dizziness, and the like).

"N/A" means not assessed.

"$(C_1-C_6)$alkyl" refers to saturated linear and branched hydrocarbon structures having 1, 2, 3, 4, 5 or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_1-C_6)$alkyl groups include methyl, ethyl, n-propyl, iso-propyl, n-butyl, tert-butyl, n-hexyl, and the like.

"(C₁-C₄)alkyl" refers to saturated linear and branched hydrocarbon structures having 1, 2, 3, or 4 carbon atoms. Examples of (C₁-C₄)alkyl groups include methyl, ethyl, n-propyl, iso-propyl, n-butyl and tert-butyl.

"(C₃-C₅)alkyl" refers to saturated linear and branched hydrocarbon structures having 3, 4, or 5 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of (C₃-C₅)alkyl groups include n-propyl, iso-propyl, n-butyl, tert-butyl, n-pentyl, and the like.

"(C₂-C₄)alkenyl" refers to a straight-chain or branched unsaturated hydrocarbon radical having 2, 3, or 4 carbon atoms and a double bond in any position, e.g., ethenyl, 1-propenyl, 2-propenyl (allyl), 1-butenyl, 2-butenyl, 3-butenyl, 1-methylethenyl, 1-methyl-1-propenyl, 2-methyl-2-propenyl, 2-methyl-1-propenyl, 1-methyl-2-propenyl, and the like.

"(C₂-C₃)alkynyl" refers to a straight chain non-cyclic hydrocarbon having 2 or 3 carbon atoms and including at least one carbon-carbon double bond. Examples of (C₂-C₃)alkenyls include -vinyl, -allyl, and 1-prop-1-enyl.

"(C₅-C₇)heterocycloalkyl" refers to a 5-, 6-, or 7-membered, saturated or unsaturated, bridged, mono- or bicyclic-heterocycle containing 1, 2, 3, or 4 ring heteroatoms each independently selected from nitrogen, oxygen, and sulfur. Examples of (C₅-C₇)heterocycloalkyl groups include pyrazolyl, pyrrolidinyl, piperidinyl, piperazinyl, tetrahydro-oxazinyl, tetrahydrofuran, thiolane, dithiolane, pyrroline, pyrrolidine, pyrazoline, pyrazolidine, imidazoline, imidazolidine, tetrazole, piperidine, pyridazine, pyrimidine, pyrazine, tetrahydrofuranone, γ-butyrolactone, α-pyran, γ-pyran, dioxolane, tetrahydropyran, dioxane, dihydrothiophene, piperazine, triazine, tetrazine, morpholine, thiomorpholine, diazepan, oxazine, tetrahydro-oxazinyl, isothiazole, pyrazolidine, and the like.

"(5- or 6-membered)heteroaryl" refers to a monocyclic aromatic heterocycle ring of 5 or 6 members, i.e., a monocyclic aromatic ring comprising at least one ring heteroatom, e.g., 1, 2, 3, or 4 ring heteroatoms, each independently selected from nitrogen, oxygen, and sulfur. Examples of -(5- or 6-membered)heteroaryls include pyridyl, pyrrolyl, furyl, imidazolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

"Halo" refers to —F, —Cl, —Br or —I.

"Sulfo-n-butyl ether derivative of β-cyclodextrin" refers to β-cyclodextrin having at least one —OH group that is derivatized by replacing the hydrogen atom thereof with —(CH₂)₄—S(O)₂—OH or —(CH₂)₄—S(O)₂—O⁻Z⁺ to provide a —O—(CH₂)₄—S(O)₂—OH or —O—(CH₂)₄—S(O)₂—O⁻Z⁺ group, respectively, where Z⁺ is a cation such as sodium, potassium, ammonium, tetramethylammonium, and the like. In one embodiment, each Z is sodium.

3.2 Methods of Using Nitroxyl Donating Compounds and Pharmaceutical Compositions Comprising them The present disclosure provides a method of administering nitroxyl therapy to a patient with an escalating dosage regimen that is believed to eliminate, minimize or reduce the risk of adverse events associated with the use of nitroxyl donating compounds. In one embodiment, the adverse event is hypotension. In one embodiment, the hypotension is clinically relevant hypotension. In another embodiment, the hypotension is symptomatic hypotension.

In one embodiment, the present disclosure provides a method of administering nitroxyl therapy to a patient comprising administering an initial dosage of a nitroxyl donating compound, or a pharmaceutical composition comprising a nitroxyl donating compound and at least one pharmaceutically acceptable excipient, in a first amount for the duration of a first period of time; optionally administering a second dosage of a nitroxyl donating compound, or a pharmaceutical composition comprising a nitroxyl donating compound and at least one pharmaceutically acceptable excipient, in a second amount for the duration of a second period of time; and administering a final dosage of a nitroxyl donating compound, or a pharmaceutical composition comprising a nitroxyl donating compound and at least one pharmaceutically acceptable excipient, in a final amount for the duration of a final period of time. In one embodiment, the sum of the first and final periods of time is at least 4 hours. In one embodiment, the sum of the first and final periods of time is at least 8 hours. In one embodiment, the sum of the first and final periods of time is at least 12 hours. In one embodiment, the sum of the first and final periods of time is at least 16 hours. In one embodiment, the sum of the first and final periods of time is at least 24 hours. In one embodiment, the sum of the first and final periods of time is at least 36 hours. In one embodiment, the sum of the first and final periods of time is at least 48 hours. In one embodiment, the sum of the first and final periods of time is at least 96 hours. In another embodiment, the sum of the first and final periods of times is about 12, 16, 24, 36, 48, 96 or 168 hours. In another embodiment, the sum of the first and final periods of times is about 24, 36 or 48 hours. In another embodiment, the sum of the first and final periods of time is about 48 hours.

In one embodiment, the first dosage amount is in the range of about 1 μg/kg/min to about 9 μg/kg/min. In another embodiment, the first dosage amount is in the range of about 2 μg/kg/min to about 8 μg/kg/min. In another embodiment, the first dosage amount is in the range of about 2 μg/kg/min to about 7 μg/kg/min. In another embodiment, the first dosage amount is in the range of about 3 μg/kg/min to about 6 μg/kg/min. In another embodiment, the first dosage amount is in the range of about 2 μg/kg/min to about 5 μg/kg/min. In another embodiment, the first dosage amount is in the range of about 2.5 μg/kg/min to about 4 μg/kg/min. In another embodiment, the first dosage amount is in the range of about 4 μg/kg/min to about 8 μg/kg/min. In another embodiment, the first dosage amount is in the range of about 5 μg/kg/min to about 7 μg/kg/min. In another embodiment, the first dosage amount is in the range of about 5.5 μg/kg/min to about 6.5 μg/kg/min. In another embodiment, the first dosage amount is about 1 μg/kg/min, about 2 μg/kg/min, about 3 μg/kg/min, about 4 μg/kg/min, about 5 μg/kg/min, about 6 μg/kg/min, about 7 μg/kg/min, about 8 μg/kg/min, or about 9 μg/kg/min. In another embodiment, the first dosage amount is about 1 μg/kg/min, about 2 μg/kg/min, about 3 μg/kg/min, about 6 μg/kg/min, or about 9 μg/kg/min. In another embodiment, the first dosage amount is about 3 μg/kg/min, about 6 μg/kg/min, or about 9 μg/kg/min. In another embodiment, the first dosage amount is about 3 μg/kg/min or about 6 μg/kg/min. In another embodiment, the first dosage amount is about 2 μg/kg/min. In another embodiment, the first dosage amount is about 3 μg/kg/min. In another embodiment, the first dosage amount is about 6 μg/kg/min.

In one embodiment, the final dosage amount is in the range of about 4 µg/kg/min to about 24 µg/kg/min. In another embodiment, the final dosage amount is in the range of about 6 µg/kg/min to about 24 µg/kg/min. In another embodiment, the final dosage amount is in the range of about 8 µg/kg/min to about 18 µg/kg/min. In another embodiment, the final dosage amount is in the range of about 10 µg/kg/min to about 14 µg/kg/min. In another embodiment, the final dosage amount is in the range of about 11 µg/kg/min to about 13 µg/kg/min. In another embodiment, the final dosage amount is in the range of about 4 µg/kg/min to about 12 µg/kg/min. In another embodiment, the final dosage amount is in the range of about 4 µg/kg/min to about 9 µg/kg/min. In another embodiment, the final dosage amount is in the range of about 4 µg/kg/min to about 6 µg/kg/min. In another embodiment, the final dosage amount is about 4 µg/kg/min, about 5 µg/kg/min, about 6 µg/kg/min, about 7 µg/kg/min, about 8 µg/kg/min, about 9 µg/kg/min, about 10 µg/kg/min, about 11 µg/kg/min, about 12 µg/kg/min, about 13 µg/kg/min, about 14 µg/kg/min, about 15 µg/kg/min, about 16 µg/kg/min, about 17 µg/kg/min, about 18 µg/kg/min, about 19 µg/kg/min, about 20 µg/kg/min, about 21 µg/kg/min, about 22 µg/kg/min, about 23 µg/kg/min, or about 24 µg/kg/min. In another embodiment, the final dosage amount is about 6 µg/kg/min, about 9 µg/kg/min, about 12 µg/kg/min, or about 16 µg/kg/min. In another embodiment, the final dosage amount is about 9 µg/kg/min, about 12 µg/kg/min, or about 16 µg/kg/min. In another embodiment, the final dosage amount is about 9 µg/kg/min or about 12 µg/kg/min. In another embodiment, the final dosage amount is about 12 µg/kg/min or about 16 µg/kg/min. In another embodiment, the final dosage amount is about 6 µg/kg/min. In another embodiment, the final dosage amount is about 9 µg/kg/min. In another embodiment, the final dosage amount is about 12 µg/kg/min. In another embodiment, the final dosage amount is about 16 µg/kg/min.

In one embodiment of the two-step escalation regimen, the first dosage amount is in the range of about 2 µg/kg/min to about 8 µg/kg/min; and the final dosage amount is in the range of about 6 µg/kg/min to about 24 µg/kg/min. In another embodiment, the first dosage amount is in the range of about 3 µg/kg/min to about 6 µg/kg/min; and the final dosage amount is in the range of about 8 µg/kg/min to about 18 µg/kg/min. In another embodiment, the first dosage amount is about 3 µg/kg/min, about 6 µg/kg/min, or about 9 µg/kg/min; and the final dosage amount is about 6 µg/kg/min, about 9 µg/kg/min, about 12 µg/kg/min, or about 16 µg/kg/min. In another embodiment, the first dosage amount is about 3 µg/kg/min; and the final dosage amount is about 6 µg/kg/min. In another embodiment, the first dosage amount is about 3 µg/kg/min; and the final dosage amount is about 12 µg/kg/min. In another embodiment, the first dosage amount is about 6 µg/kg/min; and the final dosage amount is about 12 µg/kg/min. In another embodiment, the first dosage amount is about 9 µg/kg/min; and the final dosage amount is about 12 µg/kg/min. In another embodiment, the first dosage amount is about 3 µg/kg/min; and the final dosage amount is about 16 µg/kg/min. In another embodiment, the first dosage amount is about 6 µg/kg/min; and the final dosage amount is about 16 µg/kg/min. In another embodiment, the first dosage amount is about 9 µg/kg/min; and the final dosage amount is about 16 µg/kg/min.

In one embodiment, the first period of time is in the range of about 1 hour to about 6 hours. In another embodiment, the first period of time is in the range of about 2 hours to about 6 hours. In another embodiment, the first period of time is in the range of about 3 hours to about 5 hours. In another embodiment, the first period of time is about 1 hour, 2 hours, about 3 hours, about 4 hours, about 5 hours, or about 6 hours. In another embodiment, the first time period is about 3 hours. In another embodiment, the first period of time is about 4 hours. In another embodiment, the first period of time is about 5 hours. In another embodiment, the first period of time is about 6 hours.

In one embodiment, the final period of time is at least 12 hours. In another embodiment, the final period of time is at least 16 hours. In another embodiment, the final period of time is at least 18 hours. In another embodiment, the final period of time is at least 24 hours. In another embodiment, the final period of time is at least 36 hours. In another embodiment, the final period of time is at least 48 hours. In another embodiment, the final period of time is at least 96 hours. In another embodiment, the final period of time is in the range of about 4 hours to an unlimited number of hours, determined by the duration of the treatment. In another embodiment, the final period of time is in the range of about 4 hours to about 168 hours. In another embodiment, the final period of time is in the range of about 8 hours to about 96 hours. In another embodiment, the final period of time is in the range of about 16 hours to about 48 hours. In another embodiment, the final period of time is in the range of about 24 hours to about 48 hours. In another embodiment, the final period of time is in the range of about 36 hours to about 48 hours. In another embodiment, the final period of time is about 36 hours, about 37 hours, about 38 hours, about 39 hours, about 40 hours, about 41 hours, about 42 hours, about 43 hours, about 44 hours, about 45 hours, about 46 hours, about 47 hours, or about 48 hours. In another embodiment, the final period of time is about 40 hours. In another embodiment, the final period of time is about 44 hours.

In one embodiment, the first period of time is in the range of about 2 hours to about 6 hours; and the final period of time is in the range of about 8 hours to about 96 hours. In another embodiment, the first period of time is in the range of about 3 hours to about 5 hours; and the final period of time is in the range of about 36 hours to about 48 hours. In another embodiment, the first period of time is about 1 hour, about 2 hours, about 3 hours, about 4 hours, about 5 hours, or about 6 hours; and the final period of time is about 36 hours, about 37 hours, about 38 hours, about 39 hours, about 40 hours, about 41 hours, about 42 hours, about 43 hours, about 44 hours, about 45 hours, about 46 hours, about 47 hours, or about 48 hours. In another embodiment, the first period of time is about 4 hours; and the final period of time is about 40 hours. In another embodiment, the first period of time is about 4 hours; and the final period of time is about 44 hours.

Although the present disclosure describes dose escalation regimens having two steps, it is also possible to have more steps in the same amount of time, so that the dosage escalates in smaller steps. If desired, each dose can be incrementally larger than the previous dose, or the dose can escalate every hour, every 2 hours, every 3 hours, every 4 hours, every 5 hours, every 6 hours, every 7 hours, or every 8 hours. In one embodiment, the dose escalation regimen has three steps. In another embodiment, the dose escalation regimen has four steps. In another embodiment, the dose escalation regimen has five steps. Regardless of the number of dose escalation steps, the use of an initial dosage and a final dosage in the amounts discussed above is particularly preferred.

In some embodiments, the present disclosure provides a dose escalation regimen comprising three steps. According to these embodiments, the method comprises administering an initial dosage of a nitroxyl donating compound, or a pharmaceutical composition comprising a nitroxyl donating compound and at least one pharmaceutically acceptable excipient, in a first amount for the duration of a first period of time; administering a second dosage of a nitroxyl donating compound, or a pharmaceutical composition comprising a nitroxyl donating compound and at least one pharmaceutically acceptable excipient, in a second amount for the duration of a second period of time; and administering a final dosage of a nitroxyl donating compound, or a pharmaceutical composition comprising a nitroxyl donating compound and at least one pharmaceutically acceptable excipient, in a final amount for the duration of a final period of time. In embodiments in which the escalation method comprises three steps, the initial and final doses, and the duration of their respective administrations are as described above with respect to the two-step regimen.

In one embodiment of the three-step escalation dosage regimen, the second dosage amount is in the range of about 3 µg/kg/min to about 12 µg/kg/min. In another embodiment, the second dosage amount is in the range of about 3 µg/kg/min to about 8 µg/kg/min. In another embodiment, the second dosage amount is in the range of about 5 µg/kg/min to about 7 µg/kg/min. In another embodiment, the second dosage amount is in the range of about 6 µg/kg/min to about 12 µg/kg/min. In another embodiment, the second dosage amount is in the range of about 8 µg/kg/min to about 12 µg/kg/min. In another embodiment, the second dosage amount is in the range of about 8 µg/kg/min to about 10 µg/kg/min. In another embodiment, the second dosage amount is in the range of about 10 µg/kg/min to about 12 µg/kg/min. In another embodiment, the second dosage amount is about 3 µg/kg/min, about 4 µg/kg/min, about 5 µg/kg/min, about 6 µg/kg/min, about 7 µg/kg/min, about 8 µg/kg/min, about 9 µg/kg/min, about 10 µg/kg/min, about 11 µg/kg/min, or about 12 µg/kg/min. In another embodiment, the second dosage amount is about 6 µg/kg/min, about 9 µg/kg/min, or about 12 µg/kg/min. In another embodiment, the second dosage amount is about 6 µg/kg/min or about 9 µg/kg/min. In another embodiment, the second dosage amount is about 6 µg/kg/min or about 12 µg/kg/min. In another embodiment, the second dosage amount is about 9 µg/kg/min or about 12 µg/kg/min. In another embodiment, the second dosage amount is about 6 µg/kg/min. In another embodiment, the second dosage amount is about 9 µg/kg/min. In another embodiment, the second dosage amount is about 12 µg/kg/min.

In one embodiment, the second period of time is in the range of about 1 hour to about 6 hours. In another embodiment, the second period of time is in the range of about 2 hours to about 6 hours. In another embodiment, the second period of time is in the range of about 3 hours to about 5 hours. In another embodiment, the second period of time is about 1 hour, about 2 hours, about 3 hours, about 4 hours, about 5 hours, or about 6 hours. In another embodiment, the second time period is about 3 hours. In another embodiment, the second period of time is about 4 hours. In another embodiment, the second period of time is about 5 hours. In another embodiment, the second period of time is about 6 hours.

In one embodiment, the sum of the first and the second periods of time is at least 2 hours. In another embodiment, the sum of the first and the second periods of time is at least 4 hours. In another embodiment, the sum of the first and second periods of time is at least 8 hours. In another embodiment, the sum of the first and second periods of time is at least 12 hours. In another embodiment, the sum of the first and second periods of time is at least 16 hours. In another embodiment, the sum of the first and second periods of time is at least 24 hours. In another embodiment, the sum of the first and second periods of time is at least 36 hours. In one embodiment, the sum of the first and second periods of time is at least 48 hours. In another embodiment, the sum of the first and second periods of times is about 4, 5, 6, 7, 8, 9, 10, 11, or 12 hours. In another embodiment, the sum of the first and second periods of time is about 4 hours. In another embodiment, the sum of the first and second periods of time is about 6 hours. In another embodiment, the sum of the first and second periods of time is about 8 hours. In another embodiment, the sum of the first and second periods of time is about 10 hours. In another embodiment, the sum of the first and second periods of time is about 12 hours.

In one embodiment, the first dosage amount is in the range of about 2 µg/kg/min to about 8 µg/kg/min; and the second dosage amount is in the range of about 3 µg/kg/min to about 12 µg/kg/min. In another embodiment, the first dosage amount is in the range of about 2 µg/kg/min to about 5 µg/kg/min; and the second dosage amount is in the range of about 5 µg/kg/min to about 7 µg/kg/min. In another embodiment, the first dosage amount is about 3 µg/kg/min, about 6 µg/kg/min, or about 9 µg/kg/min; and the second dosage amount is about 6 µg/kg/min, about 9 µg/kg/min, or about 12 µg/kg/min. In another embodiment, the first dosage amount is about 3 µg/kg/min; and the second dosage amount is about 6 µg/kg/min. In another embodiment, the first dosage amount is about 3 µg/kg/min; and the second dosage amount is about 9 µg/kg/min. In another embodiment, the first dosage amount is about 6 µg/kg/min; and the second dosage amount is about 9 µg/kg/min. In another embodiment, the first dosage amount is about 3 µg/kg/min; and the second dosage amount is about 12 µg/kg/min. In another embodiment, the first dosage amount is about 6 µg/kg/min; and the second dosage amount is about 12 µg/kg/min. In another embodiment, the first dosage amount is about 9 µg/kg/min; and the second dosage amount is about 12 µg/kg/min.

In one embodiment, the second dosage amount is in the range of about 3 µg/kg/min to about 8 µg/kg/min; and the final dosage amount is in the range of about 8 µg/kg/min to about 18 µg/kg/min. In another embodiment, the second dosage amount is in the range of about 5 µg/kg/min to about 7 µg/kg/min; and the final dosage amount is in the range of about 10 µg/kg/min to about 14 µg/kg/min. In another embodiment, the second dosage amount is about 6 µg/kg/min, about 9 µg/kg/min, or about 12 µg/kg/min; and the final dosage amount is the final dosage amount is about 6 µg/kg/min, about 9 µg/kg/min, about 12 µg/kg/min, or about 16 µg/kg/min. In another embodiment, the second dosage amount is about 6 µg/kg/min; and the final dosage amount is about 12 µg/kg/min. In another embodiment, the second dosage amount is about 6 µg/kg/min; and the final dosage amount is about 16 µg/kg/min. In another embodiment, the second dosage amount is about 9 µg/kg/min; and the final dosage amount is about 12 µg/kg/min. In another embodiment, the second dosage amount is about 9 µg/kg/min; and the final dosage amount is about 16 µg/kg/min. In another embodiment, the second dosage amount is about 12 µg/kg/min; and the final dosage amount is about 16 µg/kg/min.

In one embodiment, the first dosage amount is in the range of about 2 µg/kg/min to about 8 µg/kg/min; the second dosage amount is in the range of about 3 µg/kg/min to about 12 µg/kg/min; and the final dosage amount is in the range of about 8 µg/kg/min to about 18 µg/kg/min. In another embodiment, the first dosage amount is in the range of about 2 µg/kg/min to about 5 µg/kg/min; the second dosage amount is in the range of about 5 µg/kg/min to about 7

μg/kg/min; and the final dosage amount is in the range of about 10 μg/kg/min to about 14 μg/kg/min. In another embodiment, the first dosage amount is about 3 μg/kg/min, about 6 μg/kg/min, or about 9 μg/kg/min; the second dosage amount is about 6 μg/kg/min, about 9 μg/kg/min, or about 12 μg/kg/min; and the final dosage amount is about 6 μg/kg/min, about 9 μg/kg/min, about 12 μg/kg/min, or about 16 μg/kg/min. In another embodiment, the first dosage amount is about 3 μg/kg/min; the second dosage amount is about 6 μg/kg/min; and the final dosage amount is about 12 μg/kg/min. In another embodiment, the first dosage amount is about 3 μg/kg/min; the second dosage amount is about 6 μg/kg/min; and the final dosage amount is about 16 μg/kg/min. In another embodiment, the first dosage amount is about 3 μg/kg/min; the second dosage amount is about 9 μg/kg/min; and the final dosage amount is about 12 μg/kg/min. In another embodiment, the first dosage amount is about 3 μg/kg/min; the second dosage amount is about 9 μg/kg/min; and the final dosage amount is about 16 μg/kg/min. In another embodiment, the first dosage amount is about 6 μg/kg/min; the second dosage amount is about 9 μg/kg/min; and the final dosage amount is about 12 μg/kg/min. In another embodiment, the first dosage amount is about 6 μg/kg/min; the second dosage amount is about 9 μg/kg/min; and the final dosage amount is about 16 μg/kg/min. In another embodiment, the first dosage amount is about 6 μg/kg/min; the second dosage amount is about 12 μg/kg/min; and the final dosage amount is about 16 μg/kg/min.

In one embodiment, the first period of time is in the range of about 1 hour to about 6 hours; and the second period of time is in the range of about 1 hour to about 6 hours. In another embodiment, the first period of time is in the range of about 2 hours to about 6 hours; and the second period of time is in the range of about 2 hours to about 6 hours. In another embodiment, the first period of time is in the range of about 3 hours to about 5 hours; and the second period of time is in the range of about 3 hours to about 5 hours. In another embodiment, the first period of time is about 1 hour, about 2 hours, about 3 hours, about 4 hours, about 5 hours, or about 6 hours; and the second period of time is about 1 hour, about 2 hours, about 3 hours, about 4 hours, about 5 hours, or about 6 hours. In another embodiment, the first period of time is about 4 hours; and the second period of time is about 4 hours.

In one embodiment, the second period of time is in the range of about 2 hours to about 6 hours; and the final period of time is in the range of about 8 hours to about 96 hours. In another embodiment, the second period of time is in the range of about 3 hours to about 5 hours; and the final period of time is in the range of about 16 hours to about 48 hours. In another embodiment, the second period of time is about 1 hour, 2 hours, about 3 hours, about 4 hours, about 5 hours, or about 6 hours; and the final period of time is about 36 hours, about 37 hours, about 38 hours, about 39 hours, about 40 hours, about 41 hours, about 42 hours, about 43 hours, about 44 hours, about 45 hours, about 46 hours, about 47 hours, or about 48 hours. In another embodiment, the second period of time is about 4 hours; and the final period of time is about 40 hours.

In one embodiment, the first period of time is in the range of about 2 hours to about 6 hours; the second period of time is in the range of about 2 hours to about 6 hours; and the final period of time is in the range of about 8 hours to about 96 hours. In another embodiment, the first period of time is in the range of about 3 hours to about 5 hours; the second period of time is in the range of about 3 hours to about 5 hours; and the final period of time is in the range of about 16 hours to about 48 hours. In another embodiment, the first period of time is about 1 hour, about 2 hours, about 3 hours, about 4 hours, about 5 hours, or about 6 hours; the second period of time is about 1 hour, about 2 hours, about 3 hours, about 4 hours, about 5 hours, or about 6 hours; and the final period of time is about 36 hours, about 37 hours, about 38 hours, about 39 hours, about 40 hours, about 41 hours, about 42 hours, about 43 hours, about 44 hours, about 45 hours, about 46 hours, about 47 hours, or about 48 hours. In another embodiment, the first period of time is about 4 hours; the second period of time is about 4 hours; and the final period of time is about 40 hours.

In one embodiment, the patient is administered intravenously a first dosage of a nitroxyl donating compound, or a pharmaceutical composition comprising a nitroxyl donating compound and at least one pharmaceutically acceptable excipient, in an amount of about 6 μg/kg/min over about 4 hours; and then the patient is administered intravenously a second dosage of the nitroxyl donating compound, or a pharmaceutical composition comprising a nitroxyl donating compound and at least one pharmaceutically acceptable excipient, in an amount of about 12 μg/kg/min over about 44 hours.

In one embodiment, the patient is administered intravenously a first dosage of a nitroxyl donating compound, or a pharmaceutical composition comprising a nitroxyl donating compound and at least one pharmaceutically acceptable excipient, in an amount of about 3 μg/kg/min over about 4 hours; then the patient is administered intravenously a second dosage of the nitroxyl donating compound, or a pharmaceutical composition comprising a nitroxyl donating compound and at least one pharmaceutically acceptable excipient, in an amount of about 6 μg/kg/min over about 4 hours; and then the patient is administered intravenously a third dosage of a nitroxyl donating compound, or a pharmaceutical composition comprising a nitroxyl donating compound and at least one pharmaceutically acceptable excipient, in an amount of about 12 μg/kg/min over about 40 hours.

The methods of the present disclosure can be used to treat a variety of conditions that are responsive to nitroxyl therapy. For instance, the methods of the disclosure can be used to treat or prevent the occurrence of cardiovascular diseases. In certain embodiments, the methods of the disclosure can be used in the treatment cardiovascular disease, ischemia/reperfusion injury, pulmonary hypertension or another condition responsive to nitroxyl therapy. In particular embodiments, the methods of the disclosure can be used in the treatment of heart failure. In a particular embodiment, the methods of the disclosure can be used in the treatment decompensated heart failure (e.g., acute decompensated heart failure). In certain embodiments, the methods of the disclosure can be used in the treatment of systolic heart failure. In particular embodiments, the methods of the disclosure can be used in the treatment of diastolic heart failure. In particular embodiments, the methods of the disclosure can be used in the treatment of pulmonary hypertension.

In one embodiment, the methods of the disclosure can be used in the treatment of a cardiovascular disease. Examples of cardiovascular diseases and symptoms that can usefully be treated with the methods disclosed herein include cardiovascular diseases that are responsive to nitroxyl therapy, coronary obstructions, coronary artery disease (CAD), angina, heart attack, myocardial infarction, high blood pressure, ischemic cardiomyopathy and infarction, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, diastolic heart failure, systolic heart failure, congestive heart failure, acute congestive heart failure, acute decompensated heart failure, and cardiac hypertrophy.

The methods of the disclosure can be used in the treatment of heart failure. The heart failure can be of any type or form, including any of the heart failures disclosed herein. Non-limiting examples of heart failure include early stage heart failure, Class I, II, III and IV heart failure, acute heart failure, congestive heart failure (CHF) and acute congestive heart failure. In one embodiment, the methods of the disclosure can be used in the treatment of acute decompensated heart failure.

In another embodiment, the methods of the disclosure can be used in treating, preventing or delaying the onset and/or development of ischemia/reperfusion injury.

In another embodiment, the methods of the disclosure can be used to prevent or delay the onset and/or development of pulmonary hypertension. In one such embodiment, the methods of the disclosure can be used to prevent or delay the onset and/or development of pulmonary arterial hypertension (PAH).

In another embodiment, the methods of the disclosure can be used to reduce mean pulmonary arterial pressure (MPAP). In another embodiment, the MPAP is reduced by up to about 50%. In another embodiment, the MPAP is reduced by up to about 25%. In another embodiment, the MPAP is reduced by up to about 20%. In another embodiment, the MPAP is reduced by up to about 15%. In another embodiment, the MPAP is reduced by up to about 10%. In another embodiment, the MPAP is reduced by up to about 5%. In another embodiment, the MPAP is reduced to be from about 12 mmHg to about 16 mmHg. In another embodiment, the MPAP is reduced to be about 15 mmHg.

3.3 Nitroxyl Donating Compounds and Pharmaceutical Compositions Useful in the Methods of the Disclosure Table 1 provides nitroxyl donating compounds that can be used in the methods of the present disclosure.

TABLE 1

Nitroxyl Donating Compounds

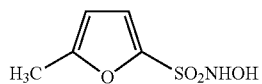

N-Hydroxy-5-methylfuran-2-sulfonamide (1)

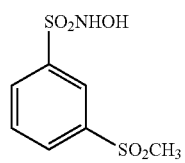

N-Hydroxy-3-methanesulfonylbenzene-1-sulfonamide (2)

TABLE 1-continued

Nitroxyl Donating Compounds

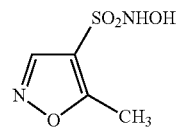

N-Hydroxy-5-methyl-1,2-oxazole-4-sulfonamide (3)

N-Hydroxy-1-benzofuran-7-sulfonamide (4)

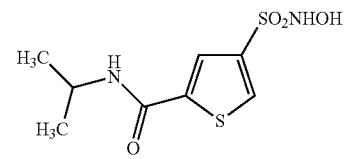

4-(Hydroxysulfamoyl)-N-(propan-2-yl)thiophene-2-carboxamide (5)

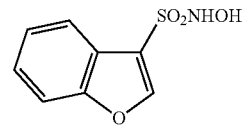

N-Hydroxy-1-benzofuran-3-sulfonamide (6)

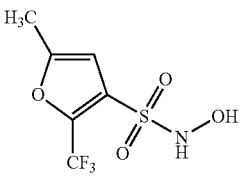

N-Hydroxy-5-methyl-2-(trifluoromethyl)furan-3-sulfonamide (7)

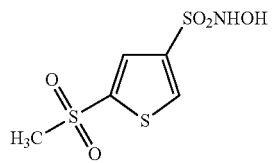

N-Hydroxy-5-methanesulfonylthiophene-3-sulfonamide (8)

TABLE 1-continued

Nitroxyl Donating Compounds

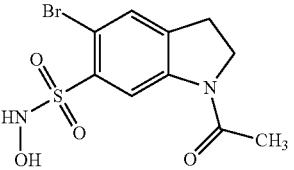

1-Acetyl-5-bromo-N-hydroxy-
2,3-dihydro-1H-indole-6-
sulfonamide (9)

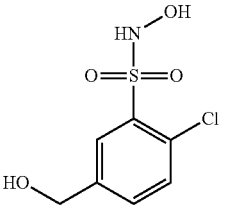

2-Chloro-N-hydroxy-5-
(hydroxymethyl)benzene-1-
sulfonamide (10)

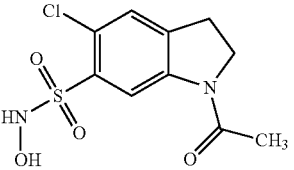

1-Acetyl-5-chloro-N-hydroxy-
2,3-dihydro-1H-indole-6-
sulfonamide (11)

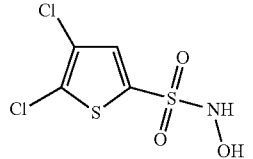

4,5-Dichloro-N-
hydroxythiophene-2-
sulfonamide (12)

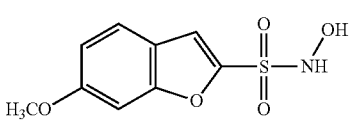

N-Hydroxy-6-methoxy-1-
benzofuran-2-sulfonamide (13)

TABLE 1-continued

Nitroxyl Donating Compounds

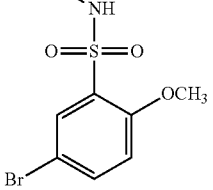

2-Fluoro-N-hydroxy-4-
methylbenzene-1-sulfonamide
(14)

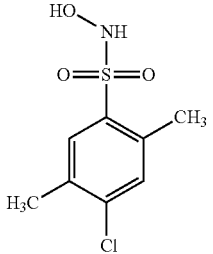

N-Hydroxy-2,1,3-
benzothiadiazole-5-
sulfonamide (15)

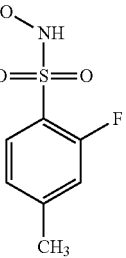

N-Hydroxy-4-
methanesulfonylthiophene-2-
sulfonamide (16)

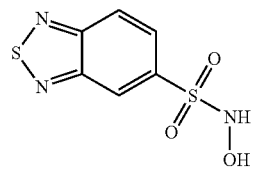

5-Bromo-N-hydroxy-2-
methoxybenzene-1-
sulfonamide (17)

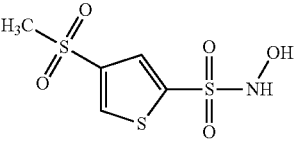

4-Chloro-N-hydroxy-2,5-
dimethylbenzene-1-
sulfonamide (18)

TABLE 1-continued

Nitroxyl Donating Compounds

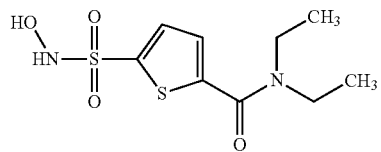

N,N-Diethyl-5-
(hydroxysulfamoyl)thiophene-
2-carboxamide (19)

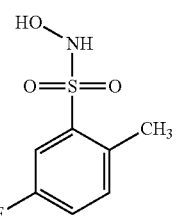

5-Fluoro-N-hydroxy-2-
methylbenzene-1-sulfonamide
(20)

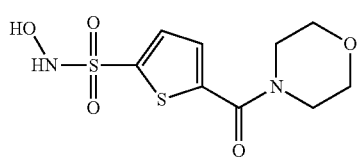

N-Hydroxy-5-(morpholine-4-
carbonyl)thiophene-2-
sulfonamide (21)

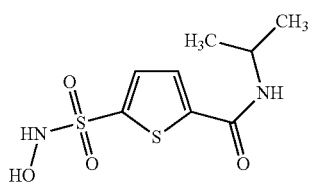

5-(Hydroxysulfamoyl)-N-
(propan-2-yl)thiophene-2-
carboxamide (22)

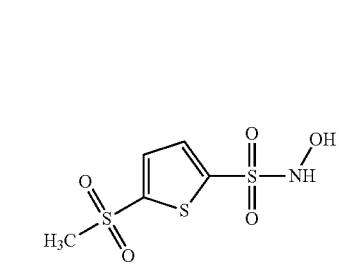

N-Hydroxy-5-methanesulfonylthiophene-2-sulfonamide (23)

TABLE 1-continued

Nitroxyl Donating Compounds

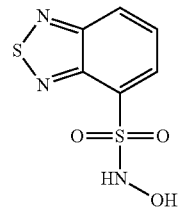

N-Hydroxy-2,1,3-
benzothiadiazole-4-sulfonamide
(24)

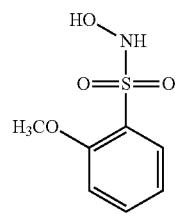

N-Hydroxy-2-methoxybenzene-
1-sulfonamide (25)

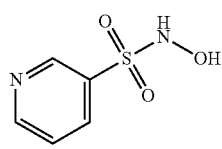

N-Hydroxypyridine-3-
sulfonamide (26)

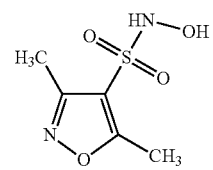

N-Hydroxy-3,5-dimethyl-1,2-
oxazole-4-sufonamide (27)

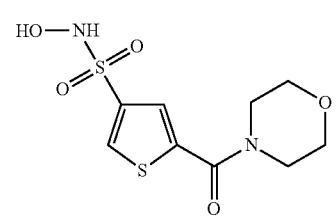

N-Hydroxy-5-(morpholine-4-
carbonyl)thiophene-3-
sulfonamide (28)

TABLE 1-continued

Nitroxyl Donating Compounds

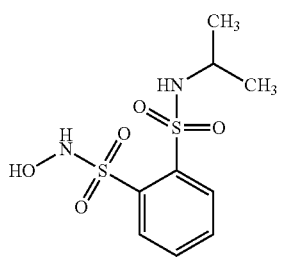

1-N-Hydroxy-2-N-(propan-2-yl)benzene-1,2-disulfonamide (29)

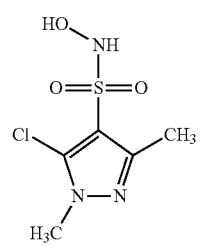

5-Chloro-N-hydroxy-1,3-dimethyl-1H-pyrazole-4-sulfonamide (30)

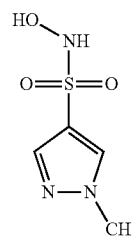

N-Hydroxy-1-methyl-1H-pyrazole-4-sulfonamide (31)

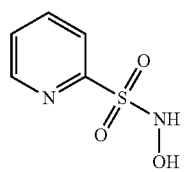

N-Hydroxypyridine-2-sulfonamide (32)

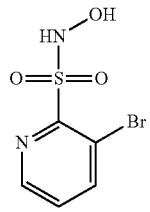

3-Bromo-N-hydroxypyridine-2-sulfonamide (33)

TABLE 1-continued

Nitroxyl Donating Compounds

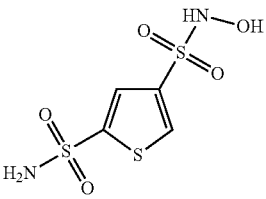

4-N-Hydroxythiophene-2,4-disulfonamide (34)

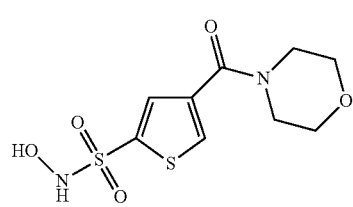

N-Hydroxy-4-(morpholine-4-carbonyl)thiophene-2-sulfonamide (35)

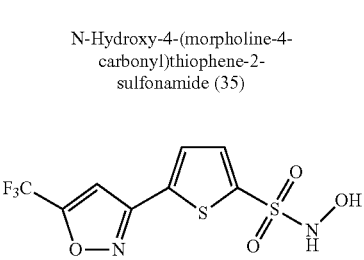

N-Hydroxy-5-[5-(trifluoromethyl)-1,2-oxazol-3-yl]thiophene-2-sulfonamide (36)

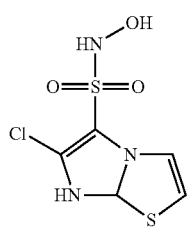

6-Chloro-N-hydroxy-7H,7aH-imidazo[2,1-b][1,3]thiazole-5-sulfonamide (37)

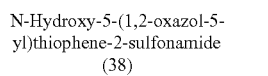

N-Hydroxy-5-(1,2-oxazol-5-yl)thiophene-2-sulfonamide (38)

TABLE 1-continued

Nitroxyl Donating Compounds

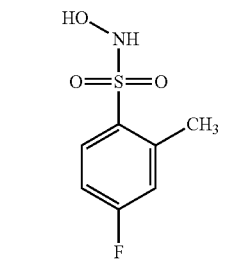

4-Fluoro-N-hydroxy-2-
methylbenzene-1-sulfonamide
(39)

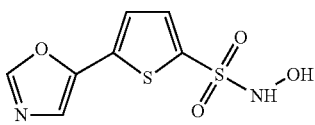

N-Hydroxy-5-(1,3-oxazol-5-
yl)thiophene-2-sulfonamide
(40)

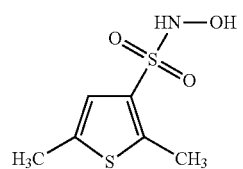

N-Hydroxy-2,5-
dimethylthiophene-3-
sulfonamide (41)

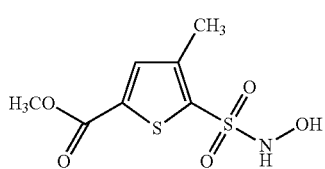

Methyl 5-(hydroxysulfamoyl)-
4-methylthiophene-2-
carboxylate (42)

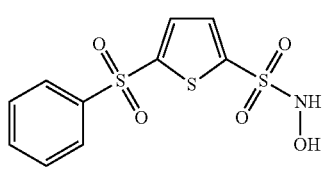

5-(Benzenesulfonyl)-N-
hydroxythiophene-2-
sulfonamide (43)

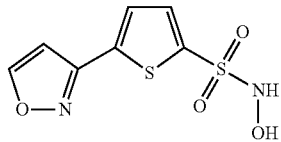

N-Hydroxy-5-(1,2-oxazol-3-
yl)thiophene-2-sulfonamide
(44)

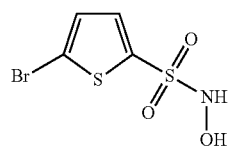

5-Bromo-N-hydroxythiophene-
2-sulfonamide (45)

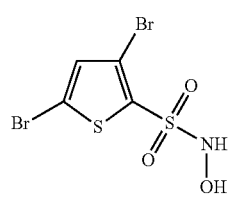

3,5-Dibromo-N-
hydroxythiophene-2-
sulfonamide (46)

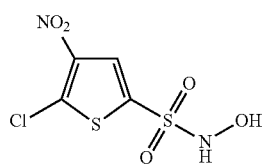

5-Chloro-N-hydroxy-4-
nitrothiophene-2-sulfonamide
(47)

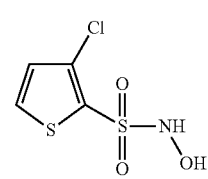

3-Chloro-N-hydroxythiophene-
2-sulfonamide (48)

TABLE 1-continued

Nitroxyl Donating Compounds

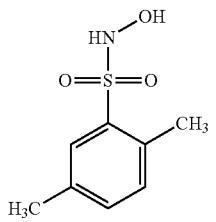

N-Hydroxy-2,5-
dimethylbenzene-1-
sulfonamide (49)

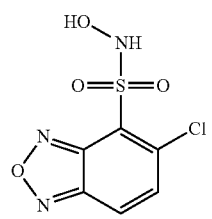

5-Chloro-N-hydroxy-2,1,3-
benzoxadiazole-4-sulfonamide
(50)

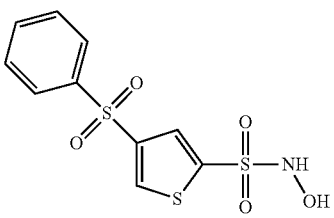

4-(Benzenesulfonyl)-N-
hydroxythiophene-2-
sulfonamide (51)

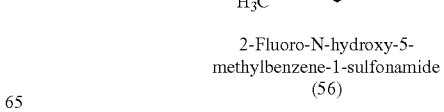

N-Hydroxy-3,4-
dimethoxybenzene-1-
sulfonamide (52)

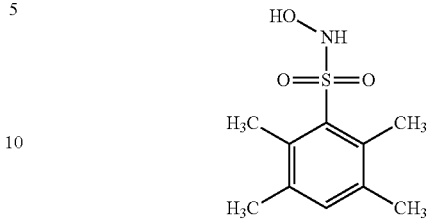

N-Hydroxy-2,3,5,6-
tetramethylbenzene-1-
sulfonamide (53)

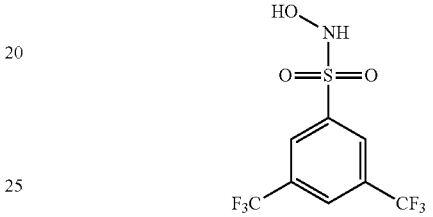

N-Hydroxy-3,5-
bis(trifluoromethyl)benzene-1-
sulfonamide (54)

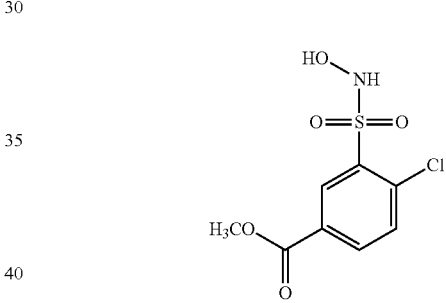

Methyl 4-chloro-3-
(hydroxysulfamoyl)benzoate
(55)

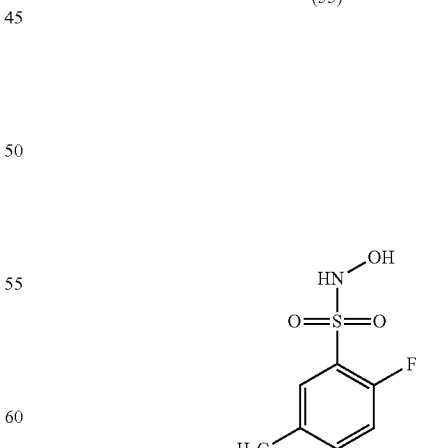

2-Fluoro-N-hydroxy-5-
methylbenzene-1-sulfonamide
(56)

TABLE 1-continued

Nitroxyl Donating Compounds

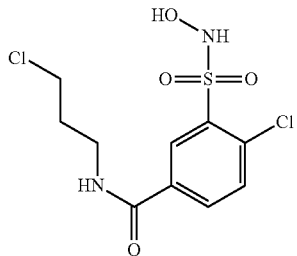

4-Chloro-N-(3-chloropropyl)-3-
(hydroxysulfamoyl)-benzamide
(57)

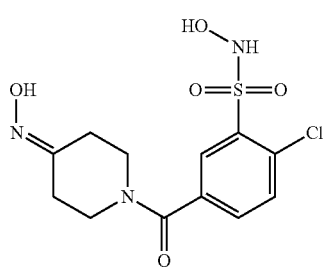

2-Chloro-N-hydroxy-5-[4-
(hydroxyimino)piperidine-1-
carbonyl]benzene-1-
sulfonamide (58)

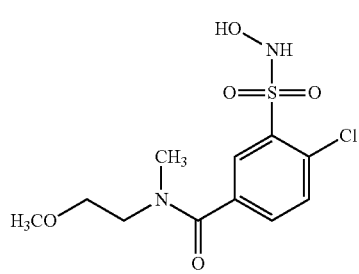

4-Chloro-3-
(hydroxysulfamoyl)-N-(2-
methoxyethyl)-N-
methylbenzamide (59)

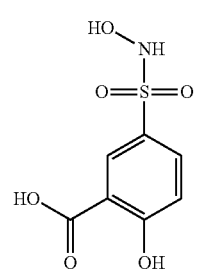

2-Hydroxy-5-
(hydroxysulfamoyl)benzoic acid
(60)

TABLE 1-continued

Nitroxyl Donating Compounds

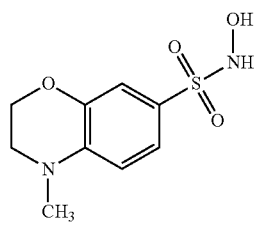

N-Hydroxy-4-methyl-3,4-
dihydro-2H-1,4-benzoxazine-7-
sulfonamide (61)

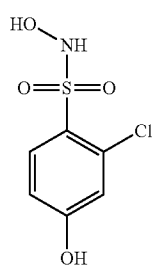

2-Chloro-N,4-
dihydroxybenzene-1-
sulfonamide (62)

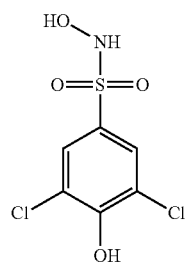

3,5-Dichloro-N,4-
dihydroxybenzene-1-
sulfonamide (63)

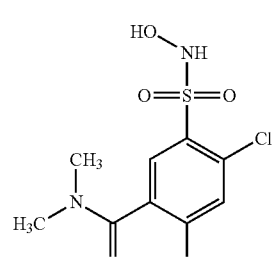

4-Chloro-2-hydroxy-5-
(hydroxysulfamoyl)-N,N-
dimethylbenzamide (64)

TABLE 1-continued

Nitroxyl Donating Compounds

5-Chloro-N-hydroxy-1-methyl-2,3-dihydro-1H-indole-6-sulfonamide (65)

2-Chloro-N,5-dihydroxybenzene-1-sulfonamide (66)

5-Bromo-N-hydroxy-1-methyl-2,3-dihydro-1H-indole-6-sulfonamide (67)

2-Chloro-N-hydroxy-5-(methoxymethyl)benzene-1-sulfonamide (68)

Methyl 5-(hydroxysulfamoyl)furan-2-carboxylate (69)

N-Hydroxy-2,5-dimethylfuran-3-sulfonamide (70)

N-Hydroxy-8-oxatricyclo[7.4.0.0]trideca-1(9),2(7),3,5,10,12-hexaene-4-sulfonamide (71)

2-(Ethanesulfonyl)-N-hydroxybenzene-1-sulfonamide (72)

N-Hydroxy-2-(propane-2-sulfonyl)benzene-1-sulfonamide (73)

4-Acetyl-N-hydroxy-3,4-dihydro-2H-1,4-benzoxazine-6-sulfonamide (74)

TABLE 1-continued

Nitroxyl Donating Compounds

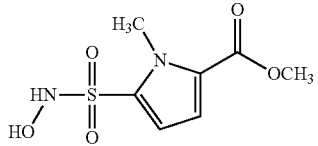

Methyl 5-(hydroxysulfamoyl)-
1-methyl-1H-pyrrole-2-
carboxylate (75)

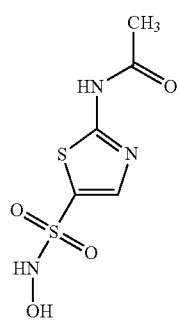

N-[5-(Hydroxysulfamoyl)-1,3-
thiazol-2-yl]acetamide (76)

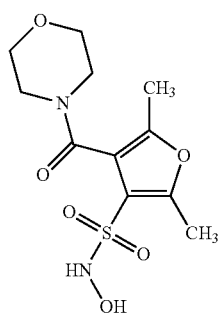

N-Hydroxy-2,5-dimethyl-4-
(morpholine-4-carbonyl)furan-
3-sulfonamide (77)

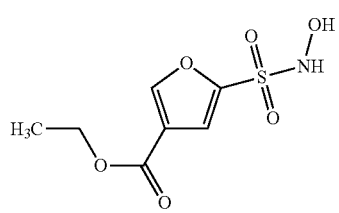

Ethyl 5-(hydroxysulfamoyl)furan-3-carboxylate
(78)

TABLE 1-continued

Nitroxyl Donating Compounds

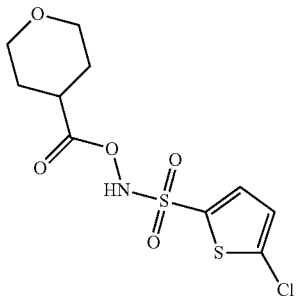

5-Chlorothiophene-2-sulfonamidooxane-4-
carboxylate (79)

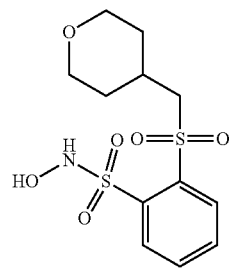

N-Hydroxy-2-(oxan-4-
ylmethanesulfonyl)benzene-
1-sulfonamide (80)

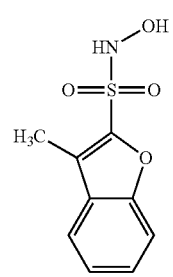

N-Hydroxy-3-methyl-1-benzofuran-
2-sulfonamide (81)

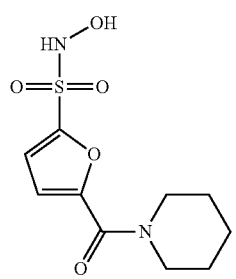

N-Hydroxy-5-(piperidine-1-
carbonyl)furan-2-sulfonamide
(82)

TABLE 1-continued

Nitroxyl Donating Compounds

N-Hydroxyfuran-2-sulfonamide (83)

N-Hydroxy-5-methylthiophene-2-sulfonamide (84)

N-Hydroxy-1-methyl-1H-pyrazole-3-sulfonamide (85)

5-Chloro-N-hydroxythiophene-2-sulfonamide (86)

3-Chloro-4-fluoro-N-hydroxybenzene-1-sulfonamide (87)

1-N,3-N-Dihydroxybenzene-1,3-disulfonamide (88)

3-Bromo-N-hydroxybenzene-1-sulfonamide (89)

TABLE 1-continued

Nitroxyl Donating Compounds

5-Fluoro-N-hydroxy-2-methylbenzene-1-sulfonamide (90)

N-Hydroxy-3,5-dimethyl-1,2-oxazole-4-sulfonamide (91)

N-Hydroxy-3-(trifluoromethoxy)benzene-1-sulfonamide (92)

N-Hydroxy-4-methanesulfonylbenzene-1-sulfonamide (93)

2,5-Dichloro-N-hydroxybenzene-1-sulfonamide (94)

TABLE 1-continued

Nitroxyl Donating Compounds 3,4-Dichloro-N-hydroxybenzene-1-sulfonamide (95)

2-(Hydroxysulfamoyl)benzoic acid (96)

3,5-Dichloro-N,2-dihydroxybenzene-1-sulfonamide (97)

In one embodiment, the nitroxyl donating compound is a compound of formula (1). In another embodiment, the nitroxyl donating compound is a compound of formula (2).

In particular embodiments, the nitroxyl donating compounds in Table 1 can be utilized as a pharmaceutically acceptable salt thereof.

In other embodiments, the nitroxyl donating compounds in Table 1 can be utilized as a prodrug thereof. Prodrugs include any compound that can be converted under physiological conditions to a nitroxyl donating compound in Table 1, such as compounds in which the N-hydroxy group of the compounds is modified to an ester, carbonate, or carbamate. In some embodiments, the N-hydroxy group of the compounds listed in Table 1 can be esterified to provide prodrugs of the compounds.

For instance, the disclosure provides the use of compounds of formula (100):

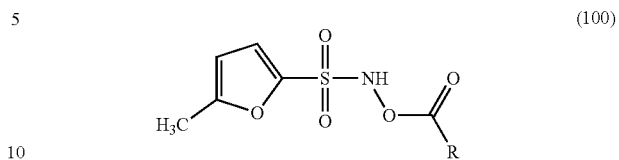

(100)

wherein R is hydrogen, —($C_1$-$C_6$)alkyl, —($C_2$-$C_4$)alkenyl, phenyl, benzyl, cyclopentyl, cyclohexyl, —($C_5$-$C_7$)heterocycloalkyl, benzyloxy, —O—($C_1$-$C_6$)alkyl, —$NH_2$, —NH—($C_1$-$C_4$)alkyl, or —N(($C_1$-$C_4$)alkyl)$_2$, wherein said —($C_1$-$C_6$)alkyl, —($C_2$-$C_4$)alkenyl, phenyl, benzyl, cyclopentyl, cyclohexyl, —($C_5$-$C_7$)heterocycloalkyl, benzyloxy, —O—($C_1$-$C_6$)alkyl, —NH—($C_1$-$C_4$)alkyl, or —N(($C_1$-$C_4$) alkyl)$_2$ can be unsubstituted or substituted with one or more substituents selected from halo, —($C_1$-$C_6$)alkyl, —($C_2$-$C_4$) alkenyl, —($C_2$-$C_3$)alkynyl, -(5- or 6-membered)heteroaryl, —O—($C_1$-$C_6$)alkyl, —S—($C_1$-$C_6$)alkyl, —C(halo)$_3$, —CH (halo)$_2$, —CH$_2$(halo), —CN, —NO$_2$, —NH$_2$, —NH—($C_1$-$C_4$)alkyl, —N(—($C_1$-$C_4$)alkyl)$_2$, —C(=O)($C_1$-$C_4$)alkyl, —C(=O)O($C_1$-$C_4$)alkyl, —OC(=O)($C_1$-$C_4$)alkyl, —OC(=O)NH$_2$, —S(=O)($C_1$-$C_4$)alkyl, or —S(=O)$_2$($C_1$-$C_4$)alkyl. In particular embodiments, R is methyl, ethyl, benzyl, or phenyl.

In particular embodiments where the nitroxyl donating compound is a compound of formula (100), R is methyl. In other embodiments where the compound has the formula (100), R is ethyl. In certain embodiments where the nitroxyl donating compound is a compound of formula (100), R is methyl or ethyl. In other embodiments where the compound has the formula (100), R is phenyl. In other embodiments where the compound has the formula (100), R is benzyl. In particular embodiments where the nitroxyl donating compound is a compound of the formula (100), R is benzyl or phenyl. In other embodiments where the compound has the formula (100), R is —NH$_2$. In each of the above embodiments in this paragraph, R is unsubstituted in one embodiment, mono-substituted in another embodiment, di-substituted with two independently selected substituents in an additional embodiment, or tri-substituted with three independently selected substituents in a further embodiment. In various embodiments of each of the above embodiments in this paragraph, the substituent is -halo, —NH$_2$, —NHCH$_3$, —CF$_3$, or —OCH$_3$ or the substituents are independently selected from -halo, —NH$_2$, —NHCH$_3$, —CF$_3$, and —OCH$_3$.

For instance, the disclosure provides the use of compounds of formula (101):

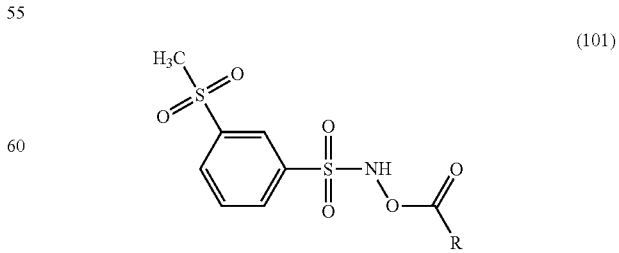

(101)

wherein R and its optional substituent(s) are as defined above with respect to the compound of formula (100).

In particular embodiments where the nitroxyl donating compound is a compound of formula (101), R is methyl. In other embodiments where the compound has the formula (101), R is ethyl. In certain embodiments where the nitroxyl donating compound is a compound of the formula (101), R is methyl or ethyl. In other embodiments where the compound has the formula (101), R is phenyl. In other embodiments where the compound has the formula (101), R is benzyl. In particular embodiments where the nitroxyl donating compound is a compound of formula (101), R is benzyl or phenyl. In other embodiments where the compound has the formula (101), R is —$NH_2$. In each of the above embodiments in this paragraph, R is unsubstituted in one embodiment, mono-substituted in another embodiment, di-substituted with two independently selected substituents in an additional embodiment, or tri-substituted with three independently selected substituents in a further embodiment. In various embodiments of each of the above embodiments in this paragraph, the substituent is -halo, —$NH_2$, —$NHCH_3$, —$CF_3$, or —$OCH_3$ or the substituents are independently selected from -halo, —$NH_2$, —$NHCH_3$, —$CF_3$, and —$OCH_3$.

The present disclosure also encompasses the use of pharmaceutical compositions comprising a nitroxyl donating compound and at least one pharmaceutically acceptable excipient. Examples of pharmaceutically acceptable excipients include those described above, such as stabilizing agents, buffering agents, carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and any combination thereof. The selection and use of pharmaceutically acceptable excipients is taught, e.g., in Troy, Ed., *Remington: The Science and Practice of Pharmacy,* 21$^{st}$ Ed. (Lippincott Williams & Wilkins, Baltimore, Md., 2005).

In various embodiments, the at least one pharmaceutically acceptable excipient comprises at least one species of cyclodextrin. In a particular embodiment, the cyclodextrin is a cyclic structure having glucose units linked by α(1-4) linkages. In another embodiment, the cyclodextrin is a β-cyclodextrin, i.e., a cyclic structure having seven glucose units linked by α(1-4) linkages. In another embodiment, the cyclodextrin is chemically modified by derivatizing any combination of the three available hydroxyl groups on each glucopyranose unit thereof.

In some embodiments where the pharmaceutically acceptable excipient comprises at least one species of cyclodextrin, the cyclodextrin is a sulfo($C_1$-$C_6$)alkyl ether derivative of β-cyclodextrin. In certain of these embodiments, the cyclodextrin is a sulfo($C_1$-$C_6$)alkyl ether derivative of β-cyclodextrin having from about six to about seven sulfo($C_1$-$C_6$) alkyl ether groups per cyclodextrin molecule. In various embodiments, the cyclodextrin is a sulfo($C_1$-$C_6$)alkyl ether derivative of β-cyclodextrin having an average of from about six to about seven sulfo($C_1$-$C_6$)alkyl ether groups per cyclodextrin molecule. In another such embodiment, the cyclodextrin is a sulfo($C_1$-$C_6$)alkyl ether derivative of β-cyclodextrin having six or seven sulfo($C_1$-$C_6$)alkyl ether groups per cyclodextrin molecule.

In a particular series of embodiments where the pharmaceutically acceptable excipient comprises at least one species of cyclodextrin, the cyclodextrin is a sulfo($C_3$-$C_5$)alkyl ether derivative of β-cyclodextrin. In one such embodiment, the cyclodextrin is a sulfo($C_3$-$C_5$)alkyl ether derivative of β-cyclodextrin having from about six to about seven sulfo($C_3$-$C_5$)alkyl ether groups per cyclodextrin molecule. In various such embodiments, the cyclodextrin is a sulfo($C_3$-$C_5$)alkyl ether derivative of β-cyclodextrin having an average of from about six to about seven sulfo($C_3$-$C_5$)alkyl ether groups per cyclodextrin molecule. In another such embodiment, the cyclodextrin is a sulfo($C_3$-$C_5$)alkyl ether derivative of β-cyclodextrin having six or seven sulfo($C_3$-$C_5$)alkyl ether groups per cyclodextrin molecule.

In particular embodiments where the pharmaceutically acceptable excipient comprises at least one species of cyclodextrin, the cyclodextrin is a sulfobutyl ether derivative of β-cyclodextrin. In certain of these embodiments, the cyclodextrin is a sulfobutyl ether derivative of β-cyclodextrin having from about six to about seven sulfobutyl ether groups per cyclodextrin molecule. In another such embodiment, the cyclodextrin is a sulfobutyl ether derivative of β-cyclodextrin having an average of from about six to about seven sulfobutyl ether groups per cyclodextrin molecule. In another such embodiment, the cyclodextrin is a sulfobutyl ether derivative of β-cyclodextrin having six or seven sulfobutyl ether groups per cyclodextrin molecule.

In certain embodiments where the pharmaceutically acceptable excipient comprises at least one species of cyclodextrin, the cyclodextrin is a sulfo-n-butyl ether derivative of β-cyclodextrin. In one such embodiment, the cyclodextrin is a sulfo-n-butyl ether derivative of β-cyclodextrin having from about six to about seven sulfo-n-butyl ether groups per cyclodextrin molecule. In another such embodiment, the cyclodextrin is a sulfo-n-butyl ether derivative of β-cyclodextrin having an average of from about six to about seven sulfo-n-butyl ether groups per cyclodextrin molecule. In another such embodiment, the cyclodextrin is a sulfo-n-butyl ether derivative of β-cyclodextrin having six or seven sulfo-n-butyl ether groups per cyclodextrin molecule.

In various particular embodiments where the pharmaceutically acceptable excipient comprises at least one species of cyclodextrin, the cyclodextrin comprises a plurality of negative charges at physiologically compatible pH values, e.g., at a pH of from about 5.0 to about 6.8 in some embodiments, from about 5.5 to about 6.5 in some embodiments, from about 5.7 to about 6.3 in some embodiments, from about 5.8 to about 6.2 in some embodiments, from about 5.9 to about 6.1 in some embodiments, and about 6.0 in particular embodiments. In one such embodiment, the at least one pharmaceutically acceptable excipient comprises CAPTISOL® cyclodextrin (Ligand Pharmaceuticals, La Jolla, Calif.).

The molar ratio between the nitroxyl donating compound and the cyclodextrin present in the composition can be from about 0.02:1 to about 2:1. In certain embodiments, the molar ratio between the nitroxyl donating compound and the cyclodextrin present in the composition can be from about 0.05:1 to about 1.5:1. In certain embodiments, the molar ratio between the nitroxyl donating compound and the cyclodextrin present in the composition can be from about 0.1:1 to about 1:1. In certain embodiments, the molar ratio between the nitroxyl donating compound and the cyclodextrin present in the composition can be from about 0.5:1 to about 1:1. In certain embodiments, the molar ratio between the nitroxyl donating compound and the cyclodextrin present in the composition can be in from about 0.7:1 to about 1:1. In certain embodiments, the molar ratio between the nitroxyl donating compound and the cyclodextrin present in the composition can be from about 0.1:1 to about 0.8:1. In certain embodiments, the molar ratio between the nitroxyl donating compound and the cyclodextrin present in the composition can be from about 0.1:1 to about 0.6:1. In certain embodiments, the molar ratio between the nitroxyl donating compound and the cyclodextrin present in the composition can be from about 0.2:1 to about 1:1. In certain embodiments, the molar ratio between the nitroxyl donating compound and the cyclodextrin present in the composition can be from about 0.2:1 to about 0.8:1. In certain embodiments, the molar ratio between the nitroxyl donating compound and the cyclodextrin present in the composition can be from about 0.4:1 to about 0.8:1. In certain embodiments, the molar ratio between the nitroxyl donating compound and the cyclodextrin present in the composition can be from about 0.4:1 to about 0.6:1. In particular embodiments, the cyclodextrin is CAPTISOL®. For the purposes of calculating molar amounts, it will be assumed that CAPTISOL® has an average molecular weight (MW) of 2163 g/mol.

In embodiments where a nitroxyl donating compound is administered parenterally (e.g., intravenously) as an aqueous composition, the cyclodextrin can be present in the composition within the range of from about 0.001% cyclodextrin (w/v) to about 10% cyclodextrin (w/v). In some embodiments, the cyclodextrin can be present in the composition within the range of from about 0.005% cyclodextrin (w/v) to about 8% cyclodextrin (w/v). In certain embodiments, the cyclodextrin can be present in the composition within the range of from about 0.010% cyclodextrin (w/v) to about 6% cyclodextrin (w/v). In certain embodiments, the cyclodextrin can be present in the composition within the range of from about 0.5% cyclodextrin (w/v) to about 8% cyclodextrin (w/v). In certain embodiments, the cyclodextrin can be present in the composition within the range of from about 1% cyclodextrin (w/v) to about 8% cyclodextrin (w/v). In certain embodiments, the cyclodextrin can be present in the composition within the range of from about 2% cyclodextrin (w/v) to about 8% cyclodextrin (w/v). In certain embodiments, the cyclodextrin can be present in the composition within the range of from about 2% cyclodextrin (w/v) to about 6% cyclodextrin (w/v). In particular embodiments, the cyclodextrin is CAPTISOL®.

Compositions comprising a nitroxyl donating compound and a cyclodextrin can be prepared as a concentrate at a particular pH. Such a concentrate can be prepared by adding the nitroxyl donating compound to an aqueous solution of the cyclodextrin at a particular pH (e.g., pH of 4). The concentrate can then be diluted into an appropriate aqueous solution (e.g., buffer) and administered to a patient. Alternatively, the concentrate comprising the nitroxyl donating compound and the cyclodextrin can be lyophilized to form a powder. The lyophilized powder can be reconstituted in the appropriate aqueous vehicle prior to administration.

The pharmaceutical compositions can be formulated for parenteral administration by, for example, subcutaneous, intramuscular, intravenous or epidural injection as, for example, a sterile solution or suspension.

In one particular embodiment, the pharmaceutical composition is formulated for intravenous administration. In another embodiment, the pharmaceutical composition is formulated for intravenous administration by continuous infusion.

Various embodiments of pharmaceutical compositions suitable for parenteral administration include, without limitation, either aqueous sterile injection solutions or non-aqueous sterile injection solutions, each containing, for example, anti-oxidants, buffers, bacteriostats and solutes that render the formulation isotonic with the blood of the intended recipient; and aqueous sterile suspensions and non-aqueous sterile suspensions, each containing, for example, suspending agents and thickening agents. The formulations can be presented in unit-dose or multi-dose containers, for example, sealed ampules or vials, and can be stored in a freeze dried (lyophilized) condition requiring only the addition of a sterile liquid carrier, such as water, immediately prior to use.

Pharmaceutical compositions administered parenterally can be administered in an acidic, neutral or basic solution. In one embodiment, pharmaceutical compositions comprising a nitroxyl donating compound can be formulated in an acidic solution having a pH of from about 4 to about 5, for instance, a pH of about 4, about 4.5, about 4.8, or about 5, including values there between. While a pH of about 4 has generally been considered optimal for formulating nitroxyl donating compositions to achieve adequate stability of the compound, it has been discovered that formulating under such acidic conditions can potentially cause or exacerbate venous irritation following parenteral administration. The amount of irritation can be attenuated by formulating the nitroxyl donating compounds in less acidic or even neutral solutions.

Accordingly, in certain embodiments, a pharmaceutical composition useful in the methods of the disclosure is formulated for parenteral injection at a pH of from about 5 to about 6.5 in some embodiments, from about 5 to about 6 in some embodiments, from about 5.5 to about 6 in some embodiments, from about 5 to about 5.5 in some embodiments, from about 5.2 to about 6.2 in some embodiments, from about 5.5 to about 6.2 in some embodiments, from about 5.8 to about 6.2 in some embodiments, and at a pH of about 6 in particular embodiments. In another embodiment a pharmaceutical composition useful in the methods of the disclosure is formulated for parenteral injection at a pH of about 5.

To achieve the desired pH of the pharmaceutical composition, a nitroxyl donor donating compound can be formulated in an aqueous buffer. For example, a nitroxyl donating compound can be formulated in a phosphate or acetate buffer. In particular embodiments, a nitroxyl donating compound is formulated in a potassium phosphate or sodium phosphate buffer. In other embodiments, a nitroxyl donating compound is formulated in a potassium phosphate buffer or sodium phosphate buffer. In other embodiments, a nitroxyl donating compound is formulated in a potassium citrate buffer or sodium citrate buffer.

The aqueous buffer can also include an appropriate sugar in order to maintain an appropriate osmolality. For instance, the pharmaceutical composition can include an appropriate amount of dextrose. The pharmaceutical compositions useful in the methods of the disclosure can be prepared by diluting a concentrate comprising a nitroxyl donating compound, optionally a cyclodextrin and an appropriate buffer into an aqueous solution comprising 5% dextrose (D5W) or 2.5% dextrose (D2.5W).

It will be apparent to those in the art that specific embodiments of the disclosed subject matter may be directed to one or more of the above- and below-indicated embodiments in any combination.

While the invention has been disclosed in some detail by way of illustration and example for purposes of clarity of understanding, it is apparent to those in the art that various changes may be made and equivalents may be substituted without departing from the true spirit and scope of the invention. Therefore, the description should not be construed as limiting the scope of the invention.

All references, publications, patents, and patent applications disclosed herein are hereby incorporated by reference in their entirety.

What is claimed is:

1. An initial dose escalation regimen method for administering nitroxyl therapy for the treatment of a cardiovascular disease to a patient having said cardiovascular disease comprising:
   administering intravenously a nitroxyl donating compound, or a pharmaceutical composition comprising the nitroxyl donating compound and at least one pharmaceutically acceptable excipient, to the patient in an amount of about 6 µg/kg/min for about 4 hours; and
   administering intravenously the nitroxyl donating compound, or the pharmaceutical composition comprising the nitroxyl donating compound and at least one pharmaceutically acceptable excipient, to the patient in an amount of about 12 µg/kg/min for about 44 hours;
   wherein the nitroxyl donating compound is a compound of formula (1):

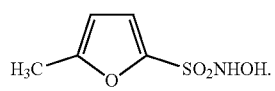

(1)

2. An initial dose escalation regimen method for administering nitroxyl therapy for the treatment of a cardiovascular disease to a patient having said cardiovascular disease comprising:
   administering intravenously a nitroxyl donating compound, or a pharmaceutical composition comprising the nitroxyl donating compound and at least one pharmaceutically acceptable excipient, to a patient in an amount of about 3 µg/kg/min for about 4 hours;
   administering intravenously the nitroxyl donating compound, or the pharmaceutical composition comprising the nitroxyl donating compound and at least one pharmaceutically acceptable excipient, to the patient in an amount of about 6 µg/kg/min for about 4 hours; and
   administering intravenously the nitroxyl donating compound, or the pharmaceutical composition comprising the nitroxyl donating compound and at least one pharmaceutically acceptable excipient, to the patient in an amount of about 12 µg/kg/min for about 40 hours;
   wherein the nitroxyl donating compound is a compound of formula (1):

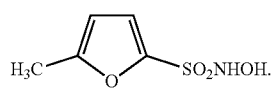

(1)

3. The method of claim 1, wherein the cardiovascular disease is heart failure.

4. The method of claim 3, wherein the cardiovascular disease is acute decompensated heart failure.

5. The method of claim 1, wherein the composition is formulated at a pH of from about 5 to about 6.

6. The method of claim 1, wherein the composition is formulated at a pH of from about 5.5 to about 6.2.

7. The method of claim 1, wherein the composition is formulated at a pH of about 6.

8. The method of claim 1, wherein the at least one pharmaceutically acceptable excipient is a buffering agent.

9. The method of claim 8, wherein the buffering agent is potassium acetate.

10. The method of claim 8, wherein the buffering agent is potassium phosphate.

11. The method of claim 1, further comprising a stabilizing agent.

12. The method of claim 11, wherein the stabilizing agent is a cyclodextrin.

13. The method of claim 12, wherein the cyclodextrin is a sulfo-n-butyl ether derivative of β-cyclodextrin having six or seven sulfo-n-butyl ether groups per cyclodextrin molecule.

14. The method of claim 12, wherein the cyclodextrin is a sulfo-n-butyl ether derivative of β-cyclodextrin, which is a β-cyclodextrin having at least one —OH group that is derivatized by replacing the hydrogen atom thereof with —$(CH_2)_4$—$S(O)_2$—$O^-Z^+$, wherein each Z is a $Na^+$.

15. The method of claim 12, wherein the molar ratio between the nitroxyl donating compound and the cyclodextrin present in the composition is from about 0.02:1 to about 2:1.

16. The method of claim 12, wherein the molar ratio between the nitroxyl donating compound and the cyclodextrin present in the composition is from about 0.05:1 to about 1.5:1.

17. The method of claim 12, wherein the molar ratio between the nitroxyl donating compound and the cyclodextrin present in the composition is from about 0.5:1 to about 1:1.

18. The method of claim 1, wherein the at least one pharmaceutically acceptable excipient is a cyclodextrin.

19. The method of claim 18, wherein the cyclodextrin is a sulfo-n-butyl ether derivative of β-cyclodextrin having six or seven sulfo-n-butyl ether groups per cyclodextrin molecule.

20. The method of claim 18, wherein the cyclodextrin is a sulfo-n-butyl ether derivative of β-cyclodextrin, which is a β-cyclodextrin having at least one —OH group that is derivatized by replacing the hydrogen atom thereof with —$(CH_2)_4$—$S(O)_2$—$O^-Z^+$, wherein each Z is a $Na^+$.

21. The method of claim 18, wherein the molar ratio between the nitroxyl donating compound and the cyclodextrin present in the composition is from about 0.02:1 to about 2:1.

22. The method of claim 18, wherein the molar ratio between the nitroxyl donating compound and the cyclodextrin present in the composition is from about 0.05:1 to about 1.5:1.

23. The method of claim 18, wherein the molar ratio between the nitroxyl donating compound and the cyclodextrin present in the composition is from about 0.5:1 to about 1:1.

24. A method of reducing the risk of hypotension in a patient having a cardiovascular disease and receiving nitroxyl therapy for the treatment of said cardiovascular disease, comprising use of an initial dose escalation regimen comprising the steps of:
   administering intravenously a nitroxyl donating compound, or a pharmaceutical composition comprising the nitroxyl donating compound and at least one pharmaceutically acceptable excipient, to the patient in an amount of about 6 µg/kg/min for about 4 hours; and
   administering intravenously the nitroxyl donating compound, or the pharmaceutical composition comprising the nitroxyl donating compound and at least one pharmaceutically acceptable excipient, to the patient in an amount of about 12 µg/kg/min for about 44 hours, wherein the patient is administered nitroxyl therapy for the treatment of a cardiovascular disease; and wherein the nitroxyl donating compound is a compound of formula (1):

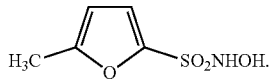

(1)

25. A method of reducing the risk of hypotension in a patient having a cardiovascular disease and receiving nitroxyl therapy for the treatment of said cardiovascular disease, comprising use of an initial dose escalation regimen comprising the steps of:

administering intravenously a nitroxyl donating compound, or a pharmaceutical composition comprising a nitroxyl donating compound and at least one pharmaceutically acceptable excipient, to a patient in an amount of about 3 µg/kg/min for about 4 hours;

administering intravenously the nitroxyl donating compound, or the pharmaceutical composition comprising the nitroxyl donating compound and at least one pharmaceutically acceptable excipient, to the patient in an amount of about 6 µg/kg/min for about 4 hours; and administering intravenously the nitroxyl donating compound, or the pharmaceutical composition comprising the nitroxyl donating compound and at least one pharmaceutically acceptable excipient, to the patient in an amount of about 12 µg/kg/min for about 40 hours, wherein the patient is administered nitroxyl therapy for the treatment of a cardiovascular disease; and wherein the nitroxyl donating compound is a compound of formula (1):

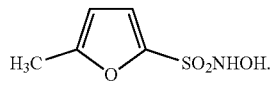

(1)

26. The method of claim 24, wherein the cardiovascular disease is heart failure.

27. The method of claim 26, wherein the cardiovascular disease is acute decompensated heart failure.

* * * * *